US010400030B2

(12) United States Patent
Edwards et al.

(10) Patent No.: US 10,400,030 B2
(45) Date of Patent: Sep. 3, 2019

(54) METHODS FOR PRODUCING OPTIMISED THERAPEUTIC MOLECULES

(71) Applicant: Crescendo Biologics Limited, Cambridge, Cambridgeshire (GB)

(72) Inventors: Bryan Edwards, Cambridge (GB); Yumin Teng, Cambridge (GB)

(73) Assignee: Crescendo Biologics Limited, Cambridge (GB)

( * ) Notice: Subject to any disclaimer, the term of this patent is extended or adjusted under 35 U.S.C. 154(b) by 23 days.

(21) Appl. No.: 15/540,400

(22) PCT Filed: Jan. 12, 2016

(86) PCT No.: PCT/GB2016/050069

§ 371 (c)(1),
(2) Date: Jun. 28, 2017

(87) PCT Pub. No.: WO2016/113556

PCT Pub. Date: Jul. 21, 2016

(65) Prior Publication Data

US 2018/0002403 A1    Jan. 4, 2018

(30) Foreign Application Priority Data

Jan. 12, 2015    (GB) .................................. 1500464.1

(51) Int. Cl.
*C40B 50/06* (2006.01)
*C07K 16/00* (2006.01)
(Continued)

(52) U.S. Cl.
CPC ............ *C07K 16/005* (2013.01); *C07K 16/00* (2013.01); *C07K 16/244* (2013.01); *C07K 16/2866* (2013.01); *C12N 15/1037* (2013.01); *C12N 15/1082* (2013.01); *C07K 2317/56* (2013.01); *C07K 2317/565* (2013.01); *C07K 2317/567* (2013.01); *C07K 2317/569* (2013.01); *C07K 2317/92* (2013.01); *C40B 50/06* (2013.01)

(58) Field of Classification Search
None
See application file for complete search history.

(56) References Cited

U.S. PATENT DOCUMENTS

| 2002/0177170 | A1 | 11/2002 | Luo et al. |
| 2003/0022240 | A1 | 1/2003 | Luo et al. |
| 2006/0099204 | A1 | 5/2006 | Couto et al. |

FOREIGN PATENT DOCUMENTS

| SG | 177012 A1 | 1/2012 |
| WO | WO 2003/000737 A1 | 1/2003 |
| WO | WO 2004/076618 A2 | 9/2004 |

OTHER PUBLICATIONS

[No Author Listed] Human Single Domain Antibodies from the Crescendo Mouse. Crescendo Biologics. Sep. 29, 2014. 1-27. Retrieved from http://www.crescendobiologics.com/uploads/Crescendo New Dev in Cancer Biologics 2014Overview 2014.09.1.pdf on Mar. 11, 2016.
(Continued)

*Primary Examiner* — Christian C Boesen
(74) *Attorney, Agent, or Firm* — Wolf, Greenfield & Sacks, P.C.

(57) ABSTRACT

The invention relates to a method of designing an immunoglobulin library for optimization of a biological property of a first lead immunoglobulin and libraries of optimized immunoglobulins produced by such methods.

10 Claims, 6 Drawing Sheets

Specification includes a Sequence Listing.

(51) Int. Cl.
*C07K 16/24* (2006.01)
*C07K 16/28* (2006.01)
*C12N 15/10* (2006.01)

(56) References Cited

OTHER PUBLICATIONS

Brüggemann et al., Human antibody production in transgenic animals. Arch Immunol Ther Exp (Warsz). Apr. 2015;63(2):101-8. doi: 10.1007/s00005-014-0322-x. Epub Dec. 3, 2014.
Chowdhury et al., Improving antibody affinity by mimicking somatic hypermutation in vitro. Nat Biotechnol. Jun. 1999;17(6):568-72.
Hanes et al., Picomolar affinity antibodies from a fully synthetic naive library selected and evolved by ribosome display. Nat Biotechnol. Dec. 2000;18(12):1287-92.
Igawa et al., Engineering the variable region of therapeutic IgG antibodies. MAbs. May-Jun. 2011;3(3):243-52. Epub May 1, 2011.
Kim et al., Mutational approaches to improve the biophysical properties of human single-domain antibodies. Biochim Biophys Acta. Nov. 2014;1844(11):1983-2001. doi: 10.1016/j.bbapap.2014.07.008. Epub Jul. 24, 2014.
Lonberg, Human antibodies from transgenic animals. Nat Biotechnol. Sep. 2005;23(9):1117-25.
Zhao et al., A bioinformatics pipeline to build a knowledge database for in silico antibody engineering. Mol Immunol. Apr. 2011;48(8):1019-26. doi:10.1016/j.molimm.2011.01.009.
PCT/GB2016/050069, Apr. 15, 2016, International Search Report and Written Opinion.

Figure 2
* BIAcore
a) Clone 1.1 IL-17A VH
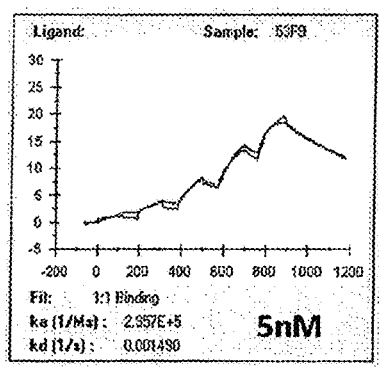
b) Clone 2.1 IL-17RA VH
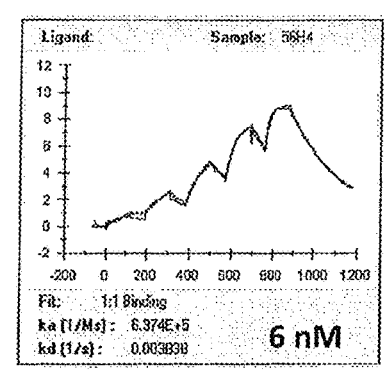

Figure 3
a.
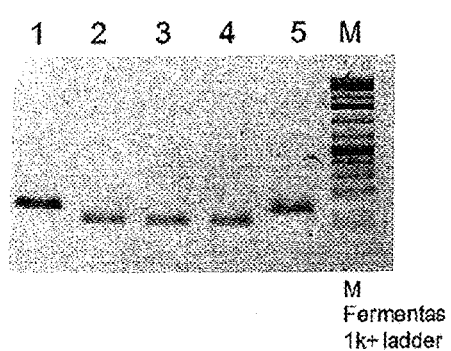
M Fermentas 1k+ ladder
b.
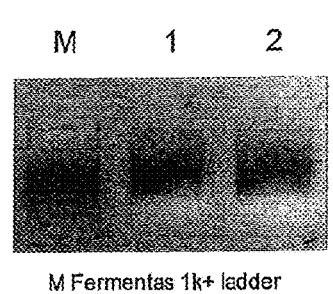
M Fermentas 1k+ ladder Figure 4: IL-17RA – Clone 2.1 VH family Figure 5
a.  M  1  2  3  4
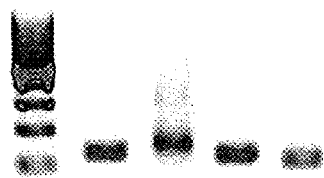
b.  M  1
M = Generuler 100bp ladder (Thermo SM0243)

METHODS FOR PRODUCING OPTIMISED THERAPEUTIC MOLECULES

RELATED APPLICATION

This application is a national stage filing under 35 U.S.C. § 371 of International Application No. PCT/GB2016/050069, filed Jan. 12, 2016, the entire contents of which is incorporated by reference herein in its entirety.

FIELD OF THE INVENTION

The present invention relates to a method of designing an immunoglobulin library, preferably an antibody library, for target optimization based on a first lead immunoglobulin. Aspects of the invention further relate to an immunoglobulin library designed by the method, and to immunoglobulins selected from the library.

BACKGROUND TO THE INVENTION

Antibody therapeutics are frequently designed by optimising an initial lead antibody in order to select desired characteristics, such as binding affinity, Kd, or lack of immunogenicity. Frequently human antibodies are generated in animals such as transgenic mice expressing human immunoglobulin genes.

After generation and isolation of a lead candidate antibody, the antibody may be optimized in various ways. Typically the lead antibody is sequenced, and the sequence used to generate an antibody library of variants for further screening. The variants may be constructed using oligonucleotides to introduce degeneracy into the coding regions (for example, the regions coding for one or more of the CDRs). The oligonucleotides may be used for PCR amplification of regions of the nucleic acids coding for the antibody. This will typically generate a large library including many variants, in which each amino acid residue in the lead is replaced with many potential substitutions. The libraries may then be cloned into expression vectors in order to generate the antibodies themselves, Display systems such as ribosome, phage or yeast display systems may be used. The antibodies thereby produced can then be screened for improvements in the desired properties.

A drawback with these known methods is that potentially far more variants are generated than will show desirable properties. This increases the time and resources necessary to generate the library and to select a variant antibody with desired characteristics. Furthermore, optimising both heavy and light chains of a fully human antibody increases the necessary workload, as well as introducing further uncertainty as to the properties of the antibody, particularly for antibodies that have both heavy and light immunoglobulin chains when assembled.

The present invention is intended to address at least some of these disadvantages, and to provide an additional method for generating immunoglobulin libraries. This is achieved in part through the effective pre-selection of certain variants by the immunised animal itself by the process of somatic hypermutation. During generation of native antibodies, proliferation of B cells is accompanied by an extremely high rate of somatic mutation in the B cell receptor locus, which generates the required antibody diversity. The mutations are mainly concentrated at certain somatic hypermutation hotspots. The present invention makes use of this native generation of diversity in order to inform the design of the immunoglobulin library.

SUMMARY OF THE INVENTION

The invention provides a method of designing an immunoglobulin library for optimization of a biological property of a first lead immunoglobulin, the method comprising:
  a) identifying one or more related immunoglobulins, said one or more related immunoglobulins being related to the first lead immunoglobulin, each immunoglobulin having been raised against a target antigen by immunisation of a transgenic non-human mammal comprising human immunoglobulin genes with the target antigen;
  b) comparing amino acid sequences of the first lead immunoglobulin and the one or more related immunoglobulins;
  c) identifying, based on the sequence comparison, one or more sites at which there are variant amino acid residues between:
  (i) the first lead immunoglobulin and the one or more related immunoglobulins, and/or
  (ii) where the one or more related immunoglobulins is a plurality of immunoglobulins, between the plurality of immunoglobulins, wherein the one or more sites at which there are variant amino acid residues comprise potential sites for modification of the first lead immunoglobulin;
  d) selecting one or more sites for modification to replace an amino acid of the first lead immunoglobulin with the corresponding variant amino acid of one or more of the related immunoglobulins, based on the sequence comparison; and
  e) generating immunoglobulin sequences for the library based on the sequence of the first lead immunoglobulin, modified at one or more of the selected sites for modification.

Preferably the immunoglobulins comprise a CDR3. The immunoglobulins may comprise a set of CDRs: CDR1, CDR2 and CDR3, preferably a set of heavy chain CDRs: HCDR1, HCDR2, and HCDR3. The immunoglobulins may consist of or comprise heavy-chain-only antibodies. The immunoglobulins may consist of or comprise $V_H$ domains.

Preferably the one or more related immunoglobulins are of common lineage and bind the same target antigen as the first lead immunoglobulin, preferably with at least 70%, 80%, 85%, 90%, or at least 95% homology in at least one CDR region when compared to the lead immunoglobulin.

By common lineage it is meant that the immunoglobulins are derived from the same germline sequence, e.g. the immunoglobulins may be obtained by somatic hypermutation of a germline sequence in non-human mammal, in particular following immunisation of the non-human mammal with a target antigen. By aligning a lead immunoglobulin sequence, e.g., a lead $V_H$ sequence, with other immunoglobulin sequences, e.g., $V_H$ sequences, of the same lineage, somatic hypermutation hot spots targeted during the immune response can be identified.

The one or more related immunoglobulins generally have at least 70% homology in CDR3 to the lead immunoglobulin, preferably at least 70%, 80%, 85%, 90%, or at least 95% homology in CDR3 to the lead immunoglobulin.

The one or more related immunoglobulins generally have at least 70% homology in CDR1 and/or CDR2 to the lead immunoglobulin, preferably at least 70%, 80%, 85%, 90%, or at least 95% homology in CDR1 and/or CDR2 to the lead immunoglobulin.

The one or more related immunoglobulins generally have at least 70% homology in the framework regions to the lead immunoglobulin, preferably at least 70%, 80%, 85%, 90%, or at least 95% homology in the framework regions to the lead immunoglobulin The one or more related immunoglobulins may comprise a plurality of related immunoglobulins comprising at least 2, 3, 4, 5, 6, 7, 8, 9, 10, 15, 20, or 25 immunoglobulins.

Step c) may comprise identifying sites for modification within a CDR of the immunoglobulin sequences, wherein a site within a CDR is considered a site for modification if there is a variant amino acid residue present in at least one, two, three, four, or five of the related immunoglobulins.

Step c) may further comprise identifying sites for modification outside a CDR of the immunoglobulin sequences, wherein a site outside a CDR is considered a site for modification if there is a variant amino acid residue present in at least 20% of the related immunoglobulins.

A potential site for modification, in particular a potential site for modification site outside a CDR which would otherwise be identified as a site for modification is not identified as a site for modification if modifying the site would lead to the introduction of one or more of the following features into the modified immunoglobulin: (i) unpaired cysteines, (ii) oxidation sites (free methionines), (iii) glycosylation sites, (iv) deamidation sites, and (v) isomerisation sites.

The sequences selected in step d) may include variant sequences reflecting each possible combination of modifications at the sites for modification.

Modification at a selected site for modification may include only a conservative amino acid substitution.

The variant immunoglobulins may include no modification outside the selected sites for modification.

Step e) may further comprise generating sequences of additional variant immunoglobulins, wherein the sequences are further modified at one or more of the selected sites for modification to replace an amino acid of the first lead immunoglobulin with a conservative amino acid replacement for the corresponding variant amino acid.

Step e) may further comprise generating sequences of additional variant immunoglobulins, wherein the sequences are further modified at one or more of the selected sites for modification to replace an amino acid of the first lead immunoglobulin with an amino acid not found at the corresponding residue of the related immunoglobulins.

The methods described herein may further comprise step f) generating an immunoglobulin library comprising immunoglobulins having the sequences generated in step e).

Libraries may be generated using various methods conventional in the art.

Method of the invention may further comprise step g) screening the immunoglobulin library to identify one or more immunoglobulins having desired biological properties.

Desired biological properties include, but are not limited to binding affinity, $IC_{50}$, good expression characteristics, solubility, stability, lack of immunogenicity/potential for generation of anti-drug antibody (ADA).

A method of the invention may comprise prior to step a), the step α) of generating and sequencing a plurality of immunoglobulins, including a first lead immunoglobulin and one or more related immunoglobulins.

The plurality of immunoglobulins may be generated by immunizing a non-human mammal, preferably a mouse or rat, preferably a transgenic mouse or rat expressing human immunoglobulin genes, with a target antigen.

A method of the invention may comprise, prior to step a), the step β) of identifying a first lead immunoglobulin.

The first lead immunoglobulin may be selected based on one or more desired biological property including, but not limited to a suitably high binding affinity for the target antigen, specificity for the target antigen, selectivity for the target antigen, ability to neutralize an effect of the target antigen, desired cross reactivity with the corresponding target antigen from other species, $IC_{50}$, good expression characteristics, solubility, stability, lack of immunogenicity/potential for ADA.

In a method of the invention the immunoglobulins may be antibodies, or antigen-binding fragments of an antibody.

The immunoglobulins may comprise or consist of heavy-chain-only antibodies.

The immunoglobulins may comprise or consist of $V_H$ domains of antibodies.

The invention provides a method of optimising a lead immunoglobulin, the method comprising:

a) performing a method of the invention described above; and b) selecting one or more optimized immunoglobulins from the library based on a desired biological property of the optimized immunoglobulin.

The invention provides a library of polynucleotides encoding a plurality of immunoglobulins, wherein the sequences of the plurality of immunoglobulins are designed in accordance with a method of the invention described above.

The invention provides a library comprising a plurality of immunoglobulins, wherein the sequences of the plurality of immunoglobulins are designed in accordance with the method of the invention described above.

The invention provides an isolated immunoglobulin designed or selected in accordance with a method of the invention described above.

The invention provides an isolated nucleic acid molecule comprising a nucleotide sequence encoding an immunoglobulin of the invention.

The invention provides an isolated polypeptide comprising an amino acid sequence of an immunoglobulin of the invention.

The invention provides a vector comprising a nucleic acid molecule of the invention.

The invention provides a plurality of vectors comprising a polynucleotide library of the invention.

The invention provides a host cell comprising a vector or vectors of the invention.

The host cell may be a bacterium, e.g., *E. coli*; a yeast, an isolated mammalian cell or cell line, e.g., a CHO or NS0 cell line.

The invention provides a method of obtaining an immunoglobulin of the invention, comprising the steps of: providing a host cell according to the invention; allowing the host cell to express the immunoglobulin encoded by the nucleic acid molecule comprised in the vector; and purifying the immunoglobulin.

The method may further comprise preparing a composition, such as a pharmaceutical formulation, comprising an immunoglobulin obtained.

The invention provides a chimeric or fusion polypeptide comprising an immunoglobulin of the invention.

The invention provides a conjugate comprising the immunoglobulin of the invention, or the chimeric or fusion polypeptide of the invention, conjugated or fused to an additional moiety.

The additional moiety may comprise one or more $V_H$ domain, preferably a human $V_H$ domain, specific for the same or a different target antigen, a cytotoxin, a radionuclide, a half-life extending moiety, e.g., a HSA or variant thereof, Fc, PEG or anti-HSA binding molecule, e.g., comprising an anti-HSA $V_H$ domain.

The invention provides a composition, such as a pharmaceutical formulation, comprising an immunoglobulin of the invention, a chimeric polypeptide of the invention or a conjugate of the invention.

BRIEF DESCRIPTION OF THE DRAWINGS

FIG. 2 shows BIAcore data showing the binding kinetics of (a) clone 1.1 and (b) clone 2.1 $V_H$ raised against the targets human IL-17A and IL-17RA respectively.

FIG. 3 shows agarose gel analysis of PCR products of nucleic acid segments for construction of a variant library based on clone 1.1 run against a marker (M) Fermentas 1K+ ladder.

FIG. 5 shows agarose gel analysis of PCR products of nucleic acid segments for construction of a variant library based on clone 2.1 run against a marker (M) generuler 100 bp ladder (ThermoSM0243).

DETAILED DESCRIPTION OF THE INVENTION

Figure 1:
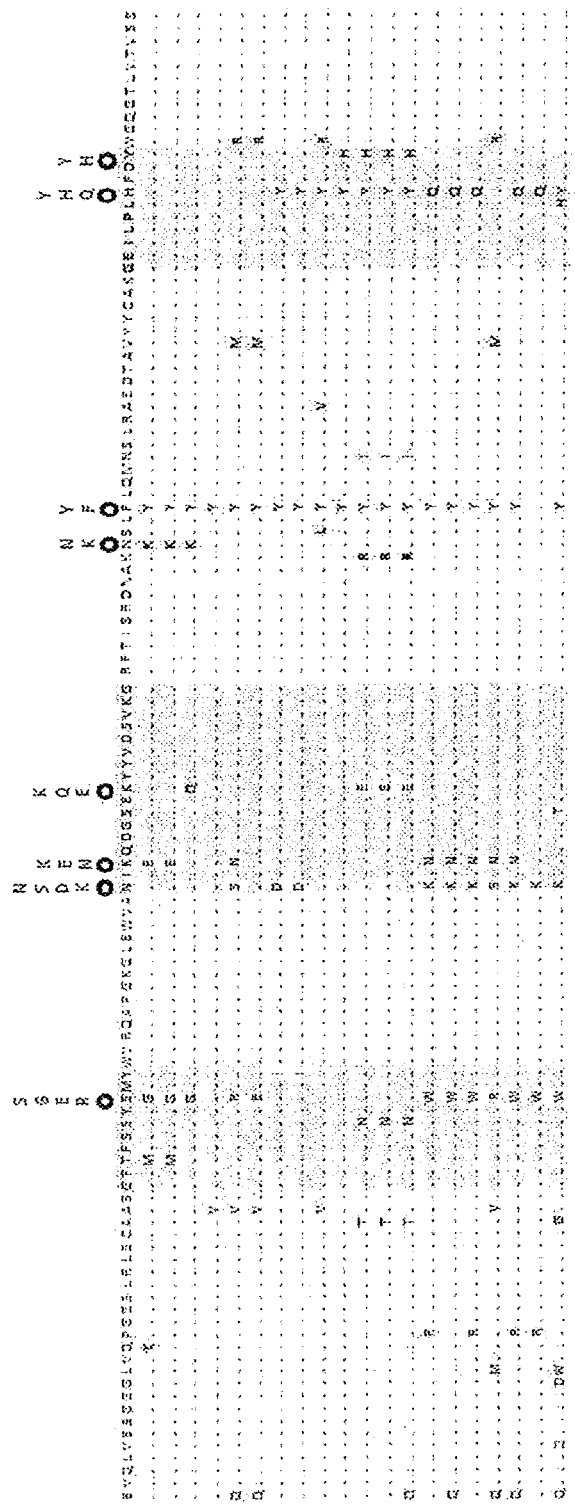
FIG. 1 shows an anti-IL-17A clone 1.1 $V_H$ family, with the sequence of the $V_H$ domain of a lead heavy-chain-only antibody candidate, clone 1.1 (top line), together with those of related antibodies. The CDR portions are shaded. The sequences provided are SEQ ID NOs: 67-87 from top to bottom.

The present invention will now be further described, with reference to specific embodiments. It will be understood that these embodiments are merely illustrative of the invention, and that the invention is as defined in the claims. Further, modifications and variations in the described embodiments will occur to the skilled person.

Generally, nomenclatures used in connection with, and techniques of, cell and tissue culture, pathology, oncology, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g., Sambrook et al., Molecular Cloning: A Laboratory Manual (2nd ed., Cold Spring Harbor Laboratory Press, Cold Spring Harbor, N.Y. (1989)). Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

The term "antibody" broadly refers to any immunoglobulin (Ig) molecule, or antigen-binding portion thereof, comprised of four polypeptide chains, two heavy (H) chains and two light (L) chains, or any functional fragment, mutant, variant, or derivative thereof, which retains the essential epitope-binding features of an Ig molecule. Such mutant, variant, or derivative antibody formats are known in the art. In a full-length antibody, each heavy chain is comprised of a heavy chain variable region (abbreviated herein as HCVR or $V_H$) and a heavy chain constant region. The heavy chain constant region is comprised of three domains, CH1, CH2 and CH3. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG3, IgG4, IgA1 and IgA2) or subclass.

Antibodies as described herein may also comprise or consist of a single domain antibody wherein said domain is a $V_H$ immunoglobulin domain. Thus, the antibody may comprise or consist of an immunoglobulin single variable domain antibody (sVD, sdAb or ISV) that has one or more $V_H$ domains, but is devoid of VL domains. Single domain antibodies have been described in the art; they are antibodies whose complementary determining regions are part of a single domain polypeptide. Preferably, the one or more $V_H$ domain is a human $V_H$ domain.

As used herein, the term VH or "variable heavy domain" refers to immunoglobulin variable heavy domains as defined by Kabat et al., Sequences of Immunological Interest, $5^{th}$ ed., U.S. Dept. Health & Human Services, Washington, D.C. (1991). The numbering and positioning of CDR amino acid residues within the variable domains is in accordance with the well-known Kabat numbering convention.

Antibodies described herein comprise an amino acid sequence and preferred sequences and/or parts thereof, such as CDRs, are defined herein.

The term "CDR" refers to the complementarity determining regions within antibody variable sequences. There are three CDRs in each of the variable regions of the heavy chain (and the light chain, when present), which are designated CDR1, CDR2 and CDR3, for each of the variable regions. The term "CDR set" refers to a group of three CDRs that occur in a single variable region capable of binding the antigen. The exact boundaries of these CDRs have been defined differently according to different systems. The system described by Kabat is preferred. The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen-binding portion thereof (Kabat et al., (1971) Ann. NY Acad. Sci. 190:382-391 and Kabat, et al., (1991) Sequences of Proteins of Immunological Interest, Fifth Edition, U.S. Department of Health and Human Services, NIH Publication No. 91-3242).

"Homology" with respect to comparison of polypeptides or polynucleotides generally refers to the percentage of amino acid (or nucleotide) residues in a first sequence that are identical with the residues of a corresponding second polypeptide (or polynucleotide), after aligning the sequences and, in some embodiments, after introducing gaps, if necessary, to achieve the maximum percent homology, and not considering any conservative substitutions as part of the sequence identity. Neither N- or C-terminal extensions, nor insertions, shall be construed as reducing identity or homology. Methods and computer programs for the alignment are well known in the art.

"Conservative amino acid substitutions" are those noted in the following table:

TABLE 1

Conservative amino acid substitutions

| Residue | Conservative substitution | Residue | Conservative substitution |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu; Val | | |

The term "Kd" refers to the "equilibrium dissociation constant" and refers to the value obtained in a titration measurement at equilibrium, or by dividing the dissociation rate constant (Koff) by the association rate constant (Kon). "KA" refers to the affinity constant. The association rate constant, the dissociation rate constant and the equilibrium dissociation constant are used to represent the binding affinity of an antibody to an antigen. Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used.

Methods for producing an immunoglobulin, given the amino acid sequence or nucleotide sequence coding for the amino acid sequence, will be known to the skilled person. Certain techniques may be used to facilitate screening of a produced immunoglobulin or immunoglobulin library; for example, a library of amino acid sequences may be displayed on a phage, phagemid, ribosome or suitable microorganism (such as yeast), such as to facilitate screening. Suitable methods, techniques and host organisms for displaying and screening (a set, collection or library of) amino acid sequences will be clear to the person skilled in the art (see for example Phage Display of Peptides and Proteins: A Laboratory Manual, Academic Press; 1st edition (Oct. 28, 1996) Brian K. Kay, Jill Winter, John McCafferty).

The immunoglobulins referred to herein can be expressed in a transgenic rodent. The transgenic rodent, for example a mouse, has a reduced capacity to express endogenous antibody genes. In one embodiment, the rodent has a reduced capacity to express endogenous light and/or heavy chain antibody genes. The rodent may therefore comprise additional modifications to disrupt expression of endogenous light and/or heavy chain antibody genes so that no functional endogenous light and/or heavy chains are produced.

The rodent may be a mouse. The mouse may comprise a non-functional endogenous lambda light chain locus. Thus, the mouse does not make a functional endogenous lambda light chain. The lambda light chain locus may be deleted in part or completely or rendered non-functional through insertion. For example, at least the constant region genes C1, C2 and C3 may be deleted or rendered non-functional through insertion. The locus may be functionally silenced so that the mouse does not make a functional lambda light chain. Furthermore, the mouse may comprise a non-functional kappa light chain locus. Thus, the mouse does not make a functional endogenous kappa light chain. The kappa light chain locus may be deleted in part or completely or rendered non-functional through insertion.

The mouse having functionally silenced endogenous lambda and kappa L-chain loci may, for example, be made as disclosed in WO 2003/000737, which is hereby incorporated by reference in its entirety.

Furthermore, the mouse may comprise a non-functional heavy chain locus. Thus, the mouse does not make a functional endogenous heavy chain. For example, as described in WO 2004/076618 (hereby incorporated by reference in its entirety), all 8 endogenous heavy chain constant region immunoglobulin genes ($\mu$, $\delta$, $\gamma3$, $\gamma1$, $\gamma2a$, $\gamma2b$, $\epsilon$ and $\alpha$) are absent in the mouse, or partially absent to the extent that they are non-functional, or genes $\delta$, $\gamma3$, $\gamma1$, $\gamma2a$, $\gamma2b$ and $\epsilon$ are absent and the flanking genes $\mu$ and $\alpha$ are partially absent to the extent that they are rendered non-functional, or genes $\mu$, $\delta$, $\gamma3$, $\gamma1$, $\gamma2a$, $\gamma2b$ and $\epsilon$ are absent and $\alpha$ is partially absent to the extent that it is rendered non-functional, or $\delta$, $\gamma3$, $\gamma1$, $\gamma2a$, $\gamma2b$, $\epsilon$ and $\alpha$ are absent and $\mu$ is partially absent to the extent that it is rendered non-functional. By deletion in part is meant that the endogenous locus gene sequence has been deleted or disrupted, for example by an insertion, to the extent that no functional endogenous gene product is encoded by the locus, i.e., that no functional product is expressed from the locus. In another embodiment, the locus is functionally silenced.

In one embodiment, the mouse comprises a non-functional heavy chain locus, a non-functional lambda light chain locus and a non-functional kappa light chain locus. The mouse therefore does not produce any functional endogenous light or heavy chains. Thus, the mouse is a triple knockout (TKO) mouse.

The transgenic mouse comprises a vector encoding and expressing a heterologous heavy chain locus. YACs are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences 2002 Macmillan Publishers Ltd, Nature Publishing Group).

Transgenic mice can be created according to standard techniques. The two most characterised routes for creating transgenic mice are via pronuclear microinjection of genetic material into freshly fertilized oocytes, or via the introduction of stably transfected embryonic stem cells into morula or blastocyst stage embryos. Regardless of how the genetic material is introduced, the manipulated embryos are transferred to pseudo-pregnant female recipients where pregnancy continues and candidate transgenic pups are born. The main differences between these broad methods are that ES clones can be screened extensively before their use to create a transgenic animal. In contrast, pronuclear microinjection relies on the genetic material integrating to the host genome after its introduction and, generally speaking, the successful incorporation of the transgene cannot be confirmed until after pups are born.

There are many methods known in the art to both assist with and determine whether successful integration of transgenes occurs. Transgenic animals can be generated by multiple means including random integration of the construct into the genome, site-specific integration, or homologous recombination. There are various tools and techniques that can be used to both drive and select for transgene integration and subsequent modification including the use of drug resistance markers (positive selection), recombinases, recombination-mediated cassette exchange, negative selection techniques, and nucleases to improve the efficiency of recombination. Most of these methods are commonly used in the modification of ES cells. However, some of the techniques may have utility for enhancing transgenesis mediated via pronuclear injection.

Further refinements can be used to give more efficient generation of the transgenic line within the desired background. As described above, in preferred embodiments, the endogenous mouse immunoglobulin expression is silenced to permit sole use of the introduced transgene for the expression of the heavy-chain-only repertoire that can be exploited for drug discovery. Genetically-manipulated mice, for example TKO mice that are silenced for all endogenous immunoglobulin loci (mouse heavy chain, mouse kappa chain and mouse lambda chain) can be used as described above. The transfer of any introduced transgene to this TKO background can be achieved via breeding, (either conventional or with the inclusion of an IVF step to give efficient scaling of the process). However, it is also possible to include the TKO background during the transgenesis procedure. For example, for microinjection, the oocytes may be derived from TKO donors. Similarly, ES cells from TKO embryos can be derived for use in transgenesis.

The immunoglobulins described herein may be conjugated to another moiety. This moiety can be selected from a toxin, enzyme or radioisotope; or a half-life extending moiety such as a HSA or PEG or an anti-HSA Ig, e.g., an anti-HSA $V_H$. The moiety can be selected from cytotoxic molecules such as chemotherapeutic drugs, bacteria and plant toxins and radionuclides. Tumor cell killing occurs upon binding of the binding molecule to a tumor cell and release and/or activation of the cytotoxic activity of the drug moiety. The selectivity afforded by drug conjugates minimizes toxicity to normal cells, thereby enhancing tolerability of the drug therapy in the patient.

Described herein are compositions, e.g., pharmaceutical compositions comprising immunoglobulins. Pharmaceutical compositions typically comprise one or more active agents (in this case, an immunoglobulin) and a pharmaceutically-acceptable carrier. The composition may be formulated depending on the desired administration route. Examples of administration routes include without limitation topical including dermal administration to or via the skin, subcutaneous or intravenous administration, oral, topical, parenteral, sublingual, rectal, vaginal, ocular, and intranasal administration. Parenteral administration includes subcutaneous injections, intravenous, intramuscular, intrasternal injection or infusion techniques. Compositions can take the form of one or more dosage units. The skilled person will be aware of suitable methods for preparing pharmaceutical formulations.

The pharmaceutically-acceptable carrier can be particulate, so that the compositions are, for example, in tablet or powder form, e.g., lyophilised, for reconstitution before use. The carrier(s) can be liquid, with the compositions being, for example, an injectable liquid. In addition, the carrier(s) can be gaseous, so as to provide an aerosol composition useful in, for example, inhalatory administration. The term "carrier" refers to a diluent, adjuvant or excipient, with which the active agent of the composition is administered. Such pharmaceutical carriers can be liquids, water or physiological saline are preferred carriers when the pharmaceutical compositions described herein are administered intravenously. Saline solutions and aqueous dextrose and glycerol solutions can also be employed as liquid carriers, particularly for injectable solutions. The compositions, if desired, can also contain minor amounts of wetting or emulsifying agents, pH buffering agents, or agents that enhance the stability and solubility of the formulation.

The composition can be in the form of a liquid, e.g., a solution, emulsion or suspension. The liquid can be useful for delivery by injection or i.v. infusion. In a composition for administration by topically to the skin or by injection or infusion, one or more of a surfactant, preservative, wetting agent, dispersing agent, suspending agent, buffer, stabilizer and isotonic agent can also be included.

The liquid compositions described herein, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides, polyethylene glycols, glycerin, or other solvents; antibacterial agents such as benzyl alcohol or methyl paraben; and agents for the adjustment of tonicity such as sodium chloride or dextrose. A parenteral composition can be enclosed in an ampoule, a disposable syringe or a multiple-dose vial made of glass, plastic or other material.

The amount of the immunoglobulin described herein that is effective/active in the treatment of a particular disorder or condition will depend on the nature of the disorder or condition, and can be determined by standard clinical techniques. In addition, in vitro or in vivo assays can optionally be employed to help to identify optimal dosage ranges. The precise dose to be employed in the compositions will also depend on the route of administration, and the seriousness of the disease or disorder, and should be decided according to the judgment of the practitioner and each patient's circumstances. The correct dosage will also vary according to the particular formulation, the mode of application, and its particular site, host and the disease being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

EXAMPLES

Heavy-chain-only antibodies comprising $V_H$ were raised against the antigens IL-17A and IL-17RA in a transgenic triple knockout mouse, which is silenced for endogenous heavy and light chain production, but which expresses exogenous human heavy chains. Two lead antibodies, clone 1.1 and clone 2.1, were obtained and used in subsequent optimization steps. The following materials and methods section gives brief details of the mouse platform used and the generation of the lead antibodies. The optimization steps and analysis are described in the examples.

Materials and Methods

Tg/TKO Mice for Immunisation

Mice carrying a heavy-chain antibody transgenic locus in germline configuration within a background that is silenced for endogenous heavy and light chain antibody expression (triple knock-out, or TKO) were created as previously described (WO2004/076618 and WO2003/000737, Ren et al. Genomics, 84, 686, 2004; Zou et al., J. Immunol., 170, 1354, 2003).

Transgenic (Tg) mice were derived following pronuclear microinjection of freshly fertilised oocytes with a yeast artificial chromosome (YAC) comprising a plethora of human $V_H$, D and J genes in combination with mouse immunoglobulin constant region genes lacking CH1 domains, mouse enhancer and regulatory regions. Yeast artificial chromosomes (YACs) are vectors that can be employed for the cloning of very large DNA inserts in yeast. As well as comprising all three cis-acting structural elements essential for behaving like natural yeast chromosomes (an autonomously replicating sequence (ARS), a centromere (CEN) and two telomeres (TEL)), their capacity to accept large DNA inserts enables them to reach the minimum size (150 kb) required for chromosome-like stability and for fidelity of transmission in yeast cells. The construction and use of YACs is well known in the art (e.g., Bruschi, C. V. and Gjuracic, K. Yeast Artificial Chromosomes, Encyclopedia of Life Sciences, 2002, Macmillan Publishers Ltd., Nature Publishing Group/els.net).

The YAC used was about 340 kb or 572 kb comprising 10 human or 23 heavy chain V genes in their natural configuration, human heavy chain D and J genes, a murine Cγ1 gene and a murine 3' enhancer gene. It lacks the $C_H1$ exon.

The transgenic founder mice were back crossed with animals that lacked endogenous immunoglobulin expression to create the Tg/TKO lines used in the immunisation studies described.

Antigen for Immunisation

The immunizations used recombinant purified protein. Recombinant human IL-17A was purchased from Peprotech (Peprotech, cat# AF-200-17). Recombinant human IL-17A was also used. Other immunogens could also have been employed and include materials such as DNA, crude protein and transfected cells.

Immunisation Protocol

Recombinant protein was administered to the Tg/TKO. Briefly, mice aged 8-12 weeks of age each received a total of 10 μg of recombinant protein, emulsified in Complete Freund's Adjuvant and delivered subcutaneously, followed by boosts of 1-10 μg of recombinant protein, emulsified in Incomplete Freund's Adjuvant, also administered subcutaneously, given at various intervals following the initial priming. A final dose of antigen was administered intraperitoneally, in phosphate-buffered saline, in the absence of adjuvant.

Alternative immunisation routes and procedures can also be employed. For example, different adjuvants or immune potentiating procedures may be used instead of Freund's adjuvant. DNA immunizations are often delivered intramuscularly or via a Genegun. Transfected cells or membrane preparations from such cells are often, although not exclusively, administered intraperitoneally.

Generation of Libraries from Immunised Mice and Cloning of Antibody $V_H$ a) Processing Tissues, RNA Extraction and cDNA Manufacture Spleen, inguinal and brachial lymph nodes were collected into RNAlater™ from each immunised animal. For each animal, ⅓ of the spleen and 4 lymph nodes were processed separately. Initially, the tissues were homogenised; following transfer of tissues to Lysing matrix D bead tubes (MP Bio cat#116913100), 600 μl of RLT buffer containing β-mercaptoethanol (from Qiagen RNeasy kit cat#74104) was added before homogenisation in a MP Bio Fastprep homogeniser (cat #116004500) using 6 m/s 40 seconds cycles. The tubes containing the homogenised tissues were transferred to ice and debris was pelleted by microcentrifugation at 10 g for 5 minutes. A sample of 400 μl of the supernatant was removed and used for RT-PCR.

Initially, RNA was extracted using Qiagen RNeasy kit cat#74104 following the manufacturer's protocol. Each RNA sample was then used to make cDNA using Superscript III RT-PCR high-fidelity kit (Invitrogen cat #12574-035). For each spleen and LN RNA sample, 5 RT-PCR reactions were performed, each with VH_J/F (long) primer in combination with a primer for $V_H1$, $V_H2$, $V_H3$, $V_H4$ or VH6 family. Details of the primers are below.

TABLE 2

| Primers. Residues in bold have homology with pUCG3 | |
|---|---|
| V1a/pelB(long) | GCCGCTGGATTGTTATTACTCGCGGCCCAGCCGG CCATGGCCCAGGTBCAGCTGGTGCAGTCTGGGGC TGAGG (SEQ ID NO: 14) |
| V2/pelB(long) | GCCGCTGGATTGTTATTACTCGCGGCCCAGCCGG CCATGGCCCAGATCACCTTGAAGGAGTCTGG (SEQ ID NO: 15) |
| V3/pelB(long) | GCCGCTGGATTGTTATTACTCGCGGCCCAGCCGG CCATGGCCSAGGTGCAGCTGGTGGAGTCTGGGGG AGG (SEQ ID NO: 16) |
| V4-4/pelB(long) | GCCGCTGGATTGTTATTACTCGCGGCCCAGCCGG CCATGGCCCAGGTGCAGCTGCAGGAGTCGGG (SEQ ID NO: 17) |
| V6/pelB(long) | GCCGCTGGATTGTTATTACTCGCGGCCCAGCCGG CCATGGCCCAGGTACAGCTGCAGCAGTCAGG (SEQ ID NO: 18) |
| VH_J/F(long) | CCGTGGTGATGGTGGTGATGGCTACCGCCACCCT CGAGTGARGAGACRGTGACC (SEQ ID NO: 19) |

Mastermixes were prepared for the RT-PCR reactions, based on the following tube reaction components.

12.5 μl 2× reaction mix
0.5 μl forward primer (10 μM)
0.5 μl reverse primer (10 μM)
0.5 μl enzyme mix
500 ng-1 μg RNA
Up to 25 μl with water The RT-PCR reactions were carried out in a thermal cycler using the following conditions:

50° C. 20 min
94° C. 2 min
35 cycles of 94° C. 15 sec
  58° C. 30 sec
  68° C. 30 sec
68° C. 5 min
Hold at 4° C.

Products in the range of 370 bp were confirmed by gel electrophoresis.

For each mouse, the $V_H$ products amplified for a given family from the ⅓ spleen and each of the 4 lymph nodes were then pooled for purification using Thermo/Fermentas GeneJet PCR purification kit (cat #K0702) which was used according to the Manufacturer's instructions, with the products eluted in 50 µl of water.

b. Cloning into Phagemid Vector

The phagemid vector, pUCG3, was employed in these studies. As indicated, $V_H$ may be cloned into pUCG3, using conventional methods involving restriction enzyme digestions with NcoI and XhoI, ligation and transformation. Alternatively, a PCR based method may be used to construct the $V_H$ phagemid libraries. Both of these procedures were used to generate libraries from the amplified $V_H$ sequences. The former method is widely used in the art and details can be found. For the PCR based method, the following procedure was used:

A linearised version of pUCG3 was created using PCR;
Primers:

```
pUCG3-F3
                                    (SEQ ID NO: 65)
CTCGAGGGTGGCGGTAGCCATCACCACCATC pUCG3-R3
                                    (SEQ ID NO: 66)
TCCATGGCCATCGCCGGCTGGGCCGCGAG
```

Phusion High fidelity PCR master mix with GC buffer (cat # F532L, NEB) was used for the PCR reactions which comprised the following reagents;

| Phusion GC 2x mix | 25 µl |
| --- | --- |
| pUCG3 | 5-10 ng |
| Primers (10 µM) | 1.25 µl of each |
| DMSO | 1.5 µl |
| Nuclease-free H₂O | to final volume of 50 µl |

The cycling conditions used were
98° C. 30 seconds
10 cycles of
98° C. 10 seconds
58° C. 20 seconds
68° C. 2 minutes, 30 seconds
20 cycles of
98° C. 10 seconds
58° C. 20 seconds
68° C. 3 minutes
68° C. 5 minutes
4° C. hold The PCR product (3152 bp) was gel purified using Fermentas GeneJet Gel purification kit (cat # K0691), according to the manufacturer's instructions, with final elution in 40 µl of elution buffer.

The purified $V_H$ RT-PCR products were employed as megaprimers with the linearised pUCG3 to give phagemid products for transformation and library creation, based on the following reactions:

| Phusion GC 2x mix | 25 µl |
| --- | --- |
| Linearised pUCG3 | 700 ng |
| VH PCR product | 250 ng |
| DMSO | 1.5 µl |

Nuclease-free H2O to 50 µl final volume
PCR was performed as follows;
98° C. 30 sec
10 cycles of: 98° C. 10 sec
58° C. 20 sec
72° C. 2 min
72° C. 5 min
Hold at 10° C.

The products of PCR were analysed on a 1% agarose gel.

The various family $V_H$/phagemid products were purified using Fermentas PCR purification kit (cat #K0702) according to the manufacturer's instructions with the final elution being in 25 µl H$_2$O and used for transformations of TG1 *E. coli* (Lucigen, Cat: 60502-2) by electroporation using Bio-Rad 10×1 mm cuvettes (BioRad cat #165-2089), an Eppendorf Eporator and pre-warmed recovery medium (Lucigen, proprietary mix). 2 µl of the purified products were added to 25 µl of cells for the electroporation, with up to 10 electroporations being performed for each $V_H$/phagemid product at 1800 v. Electroporated cells were pooled and recovered in 50 ml Falcon tubes incubated for 1 hour at 37° C. with shaking at 150 rpm. A 10-fold dilution series of an aliquot of the transformations was performed and plated in petri dishes containing 2×TY agar supplemented with 2% (w/v) glucose and 100 µg/ml ampicillin. Resulting colonies on these dishes were used to estimate the library size. The remainder of the transformation was plated on large format Bioassay dishes containing 2×TY agar supplemented with 2% (w/v) glucose and 100 µg/ml ampicillin. All agar plates were incubated overnight at 30° C. 10 ml of 2×TY broth was added to the large format bioassay dishes and colonies were scraped and OD$_{600}$ measured (OD of 1.0=5×10$^8$ cells/ml). Aliquots were stored at −80° C. in cryovials after addition of 50% v/v glycerol solution (50%) or used directly in a phage selection process.

Selection of Antibodies

Several heavy-chain-only antibodies were obtained from the immunised mice, and screened for binding affinity to the immunogen (IL-17A or IL-17RA), ability to inhibit IL-17A/IL-17RA interaction, and binding kinetics, by a combination of binding ELISA, biochemical inhibition assay, cell based inhibition assay, and BIAcore® assay, using standard techniques. From these screens, two antibodies were selected as lead antibodies—clone 1.1, raised against IL-17A, and clone 2.1, raised against IL-17RA.

BIAcore Assays.

Binding kinetics of $V_H$ antibodies were measured on a BIAcore T200 instrument. Target (either recombinant IL-17A or IL-17RA) was diluted to 1 µg/ml in acetate buffer, pH 5.5 (BIAcore, cat# BR-100-52) and coupled to a CM5 Series S chip (cat # BR-1006-68) using amine-coupling chemistry (NHS-EDC amine-coupling kit, cat # BR-1000-50) and the BIAcore immobilization Wizard software. In this way 100 RU of target was immobilised plus a blank surface (no target) was also prepared for reference subtraction.

Binding kinetics of $V_H$ antibodies were determined by single-cycle kinetics. $V_H$ antibodies were prepared in dilution series (typically 1:3 dilution series starting with 100 nM $V_H$ at the highest concentration), and then injected over the antigen-coated surfaces and also a blank surface, starting with the lowest concentration of $V_H$ and then working progressively up to the highest concentration. $V_H$ binding kinetics were then determined from the (blank subtracted) sensorgram traces using 1:1 binding models and BIAevaluation software.

Example 1. Generation of Mutagenized $V_H$ Containing Combinations of Somatic Hypermutations a. Generation of Clone 1.1 $V_H$ (Anti-IL-17A $V_H$) Variants Containing Combinations of Somatic Hypermutations A novel optimization strategy was used to increase binding affinities of $V_H$ isolated from immunised mice. Lead $V_H$ were aligned with other members of the same lineage to identify somatic hypermutation hot spots targeted during the immune response (FIG. 1). The choice of amino acids at these positions formed the basis of a new recombination library approach, and led to the design of new libraries aimed at selecting higher affinity $V_H$ with optimal amino acids at each mutation hot spot.

As an example for IL-17A, clone 1.1 was isolated directly from an immunised Tg/TKO mouse as described above. This $V_H$ was shown to bind IL-17A with high affinity (FIG. 2). Alignment of $V_H$ clone 1.1 with other members of the same lineage identified a number of amino acid positions that had been mutated during the immune response, and both $V_H$-CDRs and $V_H$-framework regions were affected (FIG. 1). This information was then utilised to design a new clone 1.1 recombination library with the aim of identifying a higher affinity variant of $V_H$ clone 1.1.

Phusion High fidelity PCR master mix with HF buffer (cat # F531L, Thermo) was used for the PCR reactions which were set up for each primer pairing as follows:

| | |
|---|---|
| Phusion HF 2x mix | 25 μl |
| Primers (10 μM) | 1.25 μl each (pairings as in table) |
| clone 1.1 plasmid DNA (34 ng/μl) | 0.5 μl |
| Nuclease-free H₂O | to 50 μl final volume |

PCR was performed as follows;
98° C. 30 sec
31 cycles: 98° C. 10 sec
    58° C. 20 sec
    72° C. 20 sec
72° C. 10 min
Hold at 10° C.

The products of each PCR were analysed on a 1% agarose gel (FIG. 3 (a)). Each product was then purified using Fermentas PCR purification kit (K0701) into 40 μl elution buffer. Assembly PCRs were then set up to rebuild the full $V_H$ sequence:

| | |
|---|---|
| Phusion HF 2x mix | 25 μl |
| Purified PCR product 1 | 5 μl |

TABLE 3

Primers

| PCR | Primer | Sequence | Amino acid changes (Kabat position) | PCR product size |
|---|---|---|---|---|
| 1 | V3/pelB(long) | GCCGCTGGATTGTTATTACTCGCG GCCCAGCCGGCCATGGCCSAGGT GCAGCTGGTGGAGTCTGGGGGAG G (SEQ ID NO: 20) | none | 160 bp |
| | clone 1.1-33S-R | TGGCGGACCCAGTACATNYBATAA CTACTAAAGGTG (SEQ ID NO: 21) | S33 to S, G, E, R | |
| 2 | clone 1.1-33S-F | CACCTTTAGTAGTTATVRNATGTA CTGGGTCCGCCA (SEQ ID NO: 22) | S33 to S, G, E, R | 100 bp |
| | clone 1.1-57K-R | CACATAGTATTBCTCACTTCCATCT TGNTYTATSYYGGCCACCCACTCC AG (SEQ ID NO: 23) | N50 to N, S, D, K K52 to K, E, N K57 to K, Q, E | |
| 3 | clone 1.1-57K-F | CAAGATGGAAGTGAGVAATACTAT GTGGACTCTGTGA (SEQ ID NO: 24) | K57 to K, Q, E | 100 bp |
| | clone 1.1-76/79-R | AGGCTATTCATTTGCAGAWACAGT GASTTCTTGGCGTTGTCTCTG (SEQ ID NO: 25) | N76 to N, K F79 to F, Y | |
| 4 | clone 1.1-76/79-F | CAGAGACAACGCCAAGAASTCACT GTWTCTGCAAATGAATAGCCT (SEQ ID NO: 26) | N76 to N, K F79 to F, Y | 90 bp |
| | clone 1.1-89V-R | AGTATTTCCCCTTTCGCACAGTAA TACACAGCCGTG (SEQ ID NO: 27) | none | |
| 5 | clone 1.1-89V-F(long) | CACGGCTGTGTATTACTGTGCGAA AGGGGAAATACTACCCCTCYASTT TGACYACTGGGGCCAGGGA (SEQ ID NO: 28) | H100A to H, Y, Q Y100D to Y, H | 130 bp |
| | VH_J/F(long) | CCGTGGTGATGGTGGTGATGGCT ACCGCCACCCTCGAGTGARGAGA CRGTGACC (SEQ ID NO: 29) | none | |

| | |
|---|---|
| Purified PCR product 2 | 5 µl |
| Purified PCR product 3 | 5 µl |
| Purified PCR product 4 | 5 µl |
| Purified PCR product 5 | 5 µl |

Figure 4:
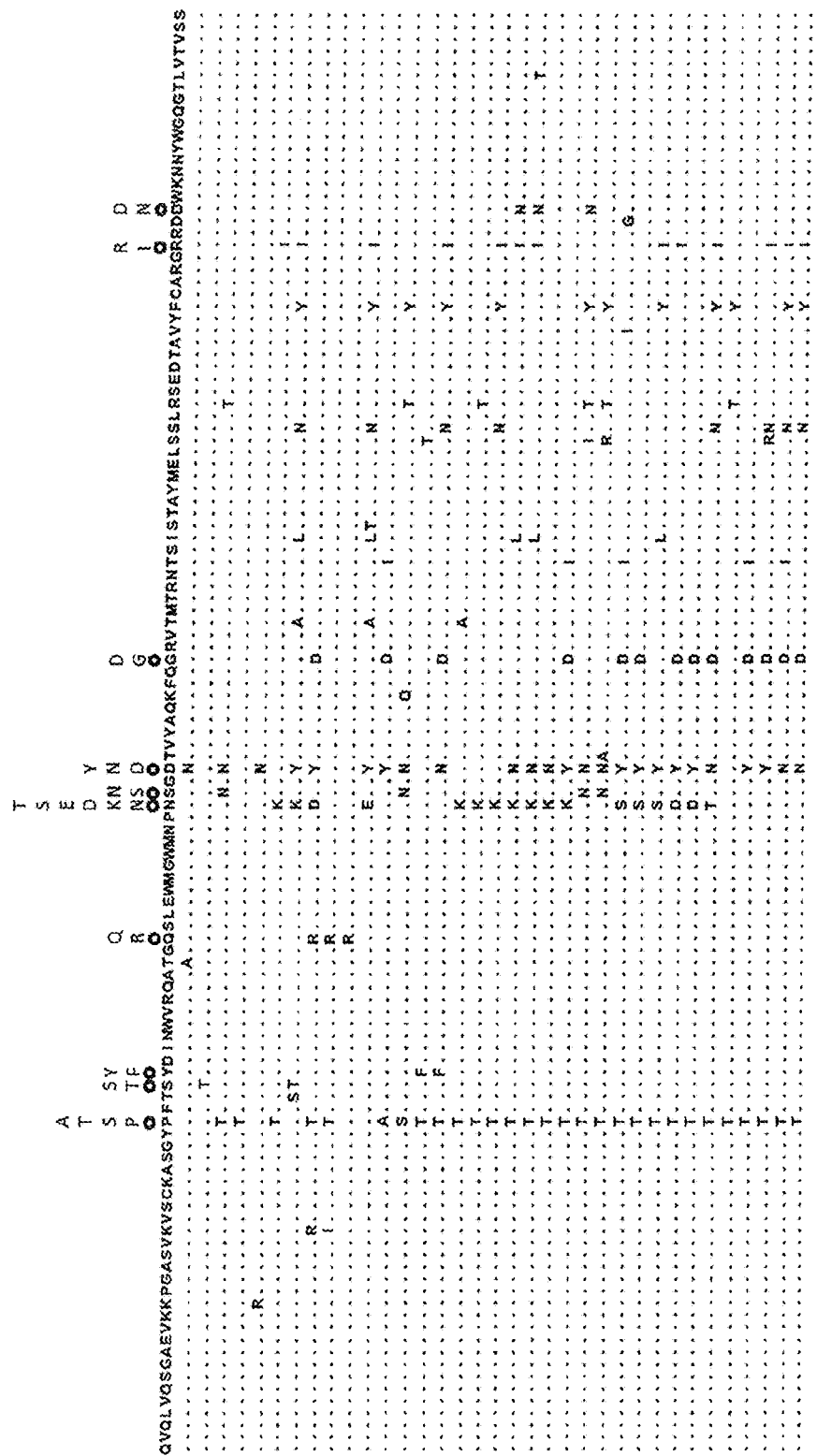
FIG. 4 shows the sequence of the $V_H$ domain of a lead heavy chain only antibody candidate, clone 2.1 (top line), together with those of related antibodies. The CDR portions are shaded. The sequences provided are SEQ ID NOs: 88-123 from top to bottom.

PCR was performed as follows;
98° C. 30 sec
5 cycles: 98° C. 10 sec
    58° C. 20 sec
    72° C. 20 sec 0.5 µl of primers V3/pelB(long) and $V_H$_J/F(long) (both 10 µM) were added to the reaction and then continued for a further 10 PCR cycles at the above conditions. The PCR product was analysed on a 1% agarose gel (FIG. 3 (*b*)) and purified using Fermentas PCR purification kit into 40 µl elution buffer. The PCR product was then used as a mega-primer for library construction as described in Example 2.

b. Generation of Clone 2.1 $V_H$ (Anti-IL-17RA) Variants Containing Combinations of Somatic Hypermutations A similar recombination library approach was also used for the anti-IL-17RA lineage headed up by $V_H$ clone 2.1. This $V_H$ was shown to bind IL-17RA with high affinity (FIG. 2). Alignment of clone 2.1 with other members of the same lineage identified a number of amino acid positions that had been mutated during the immune response (FIG. 4). This information was then utilised to design a new clone 2.1 recombination library with the aim of identifying a higher affinity variant of clone 2.1.

| | |
|---|---|
| Thermo) | |
| Primers (10 µM) | 1 µl each (pairings as in table) |
| clone 2.1 plasmid DNA | 20 ng |
| Nuclease-free H$_2$O | to 50 µl final volume |

PCR was performed as follows;
94° C. 60 sec
30 cycles: 94° C. 30 sec
    58° C. 30 sec
    72° C. 30 sec
72° C. 5 min
Hold at 10° C.

The products of each PCR were analysed on a 1% agarose gel (FIG. 5 (*a*)). Each product was then purified using Fermentas PCR purification kit (K0701). Assembly PCRs were then set up to rebuild the full VH sequence:

| | |
|---|---|
| Phusion HF 5x buffer | 10 µl |
| 25 mM dNTPs (cat # R0182, Thermo) | 1 µl |
| pUCG3-VH-F primer (10 µM) | 1 µl |
| pUCG3-VH-R primer (10 µM) | 1 µl |
| Purified PCR product 1 | 5 µl |
| Purified PCR product 2 | 5 µl |
| Purified PCR product 3 | 5 µl |
| Purified PCR product 4 | 5 µl |
| Nuclease-free H$_2$O | to 50 µl final volume |

TABLE 4

Primers

| PCR | Primer | Sequence | Amino acid changes (Kabat position) | PCR product size |
|---|---|---|---|---|
| 1 | pUCG3-VH-F | GGATTGTTATTACTCGCGGCCCAG (SEQ ID NO: 1) | none | 100 bp |
| | B clone 2.1 | CTGGTGAAGGNGTATCCAGAAGCC TTGC (SEQ ID NO: 2) | P28 to S, P, T, A | |
| 2 | C clone 2.1 | GCAAGGCTTCTGGATACNCCTTCA CCASTTVVTGATATCAATTGGGTGC GACAGGCCACAGGACRAAGCCTTG AGTGGATGGGATGGATGAACC (SEQ ID NO: 3) | P28 to S, P, T, A<br>S30 to S or T<br>Y31 to Y or F<br>Q43 to Q or R | 150 bp |
| | D clone 2.1 | CCTGGTCATGGTGACTCTGYCCTG GAATTTCTGTGCATAGACTGTGTHA CCAYTBBYAGGGTTCATCCATCCCA TCCAC (SEQ ID NO: 4) | N54 to T, S, E, D, K, N<br>S55 to S or N<br>D57 to Y, N, D<br>G66 to G or D | |
| 3 | G clone 2.1 | GGCAGAGTCACCATGACCAGGAA (SEQ ID NO: 5) | none | 120 bp |
| | F clone 2.1 | GTTCTTCCAGTYATCCCTTMTGCCT CTCGCAC (SEQ ID NO: 6) | R100 to R or I<br>D104 to N or D | |
| 4 | E clone 2.1 | GTGCGAGAGGCAKAAGGGATRACT GGAAGAAC (SEQ ID NO: 7) | R100 to R or I<br>D104 to N or D | 100 bp |
| | pUCG3-VH-R | CCGTGGTGATGGTGGTGATG (SEQ ID NO: 8) | none | |

Phusion High fidelity DNA polymerase (cat # F518, Thermo) was used for the PCR reactions which were set up for each primer pairing as follows:

| | |
|---|---|
| Phusion HF 5x buffer | 10 µl |
| 25 mM dNTPs (cat # R0182, | 1 µl |

94° C. 60 sec
30 cycles: 94° C. 30 sec
    58° C. 30 sec
    72° C. 30 sec
72° C. 5 min
Hold at 10° C.

The PCR product was analysed on a 1% agarose gel (FIG. 5 (*b*)) and purified using Fermentas PCR purification kit into 40 µl elution buffer. The PCR product was then used as a megaprimer for library construction as described in Example 2.

Example 2. Generation of Phage Display Libraries of Mutagenised Clone 1.1 and Clone 2.1 $V_H$ A PCR-based method was used to construct $V_H$ phagemid libraries containing clone 1.1 and clone 2.1 mutagenized sequences. The purified $V_H$ assembly PCR products (from Example 1) were employed as megaprimers with linearised pUCG3 phagemid vector to give products for transformation and library creation, based on the following reactions;

| | |
|---|---|
| Phusion GC 2x mix | 25 µl |
| Linearised pUCG3 | 700 ng |
| $V_H$ PCR product | 250 ng |
| DMSO | 1.5 µl |
| Nuclease-free H$_2$O | to 50 µl final volume |

PCR was performed as follows;
98° C. 30 sec
10 cycles: 98° C. 10 sec
 58° C. 20 sec
 72° C. 2 min
72° C. 5 min
Hold at 10° C.

The $V_H$/phagemid PCR products were purified using Fermentas PCR purification kit (cat #K0702) according to the manufacturer's instructions with the final elution being in 25 µl H$_2$O. The purified $V_H$/phagemid PCR products were used for transformations of TG1 E. coli (Lucigen, Cat: 60502-2) by electroporation using BioRad 10×1 mm cuvettes (BioRad cat #165-2089), an Eppendorf Eporator and pre-warmed recovery medium (Lucigen, proprietary mix). 2 µl of the purified products were added to 25 µl of cells for the electroporation, with up to 10 electroporations being performed for each $V_H$/phagemid product at 1800 v. Electroporated cells were pooled and recovered in 50 ml Falcon tubes incubated for 1 hour at 37° C. with shaking at 150 rpm. A 10-fold dilution series of an aliquot of the transformations was performed and plated in petri dishes containing 2×TY agar supplemented with 2% (w/v) glucose and 100 µg/ml ampicillin. Resulting colonies on these dishes were used to estimate the library size. The remainder of the transformation was plated on large format Bioassay dishes containing 2×TY agar supplemented with 2% (w/v) glucose and 100 µg/ml ampicillin. All agar plates were incubated overnight at 30° C. 10 ml of 2×TY broth was added to the large format bioassay dishes, colonies were scraped and OD$_{600}$ measured (OD of 1.0=5×10$^8$ cells/ml). Aliquots were stored at −80° C. in cryovials after addition of 50% v/v glycerol solution (50%) or used directly in phage display selections.

In some instances, clones were picked directly and sequence was determined to give an estimate of the diversity of the library. For both clone 1.1 and clone 2.1, phage display libraries with greater than 1e8 (1×10$^8$) recombinants were constructed to fully capture the $V_H$ diversity generated by the mutagenic PCR reactions.

Example 3. Phage Display Selections of Mutagenised Clone 1.1 and Clone 2.1 $V_H$ Libraries Preparation of library phage stocks and phage display selections were performed according to published methods (Antibody Engineering, edited by Benny Lo, chapter 8, p 161-176, 2004). In most cases, phage display combined with a panning approach was used to isolate binding $V_H$ domains. However, a variety of different selection methods are well described in the art, including soluble selections, selections performed under stress (e.g. heat) and competitive selections, where excess antigen or antigen-reactive $V_H$ domains are added as competition to encourage the recovery of high affinity $V_H$ domains or to skew selections away from a particular epitope.

For both clone 1.1 and clone 2.1 recombination libraries, one round of panning selection was performed (antigen immobilised onto maxisorb plates (Nunc 443404) in 50 µl volumes at 10 ug/ml in PBS), followed by 2-3 rounds of soluble selection using reducing amounts of antigen at successive rounds of selection (1 nm down to 100 pM of biotinylated antigen).

Example 4. Identification of $V_H$ with Improved Binding Affinities $V_H$ from the different selections were screened using a BIAcore T200 instrument to identify $V_H$ with improved binding affinities.

Recombinant IL-17A (Peprotech AF-200-17) was diluted to 1 µg/ml in acetate buffer, pH 5.5 (BIAcore, cat# BR-100-52) and coupled to a CM5 Series S chip (cat # BR-1006-68) using amine-coupling chemistry (NHS-EDC amine-coupling kit, cat # BR-1000-50) and the BIAcore immobilization Wizard software. In this way 100 RU of IL-17A was immobilised plus a blank surface (no IL-17A) was also prepared for reference subtraction. For IL-17RA, first a protein G chip was prepared by diluting protein G to 20 µg/ml in acetate buffer, pH 4 (BIAcore, cat# BR-100-49) and then coupled 1200 RU a CM5 Series S chip using amine coupling chemistry. This surface was then used to capture IL-17RA Fc fusion protein from solution: IL-17RA at 10 µg/ml in HBS injected for 10 seconds at 30 µl/min flow rate would capture approximately 100-150 RU of IL-17RA onto the protein G surface.

Binding kinetics of optimized clone 1.1 (anti-IL-17A) and clone 2.1 (anti-IL-17RA) $V_H$ were determined by single-cycle kinetics. $V_H$ were prepared in dilution series (typically 1:3 dilution series starting with 100 nM $V_H$ at the highest concentration), and then injected over the antigen-coated surfaces and also a blank surface, starting with the lowest concentration of $V_H$ and then working progressively up to the highest concentration. $V_H$ binding kinetics were then determined from the (blank subtracted) sensorgram traces using 1:1 binding models and BIAevaluation software.

Figure 6:
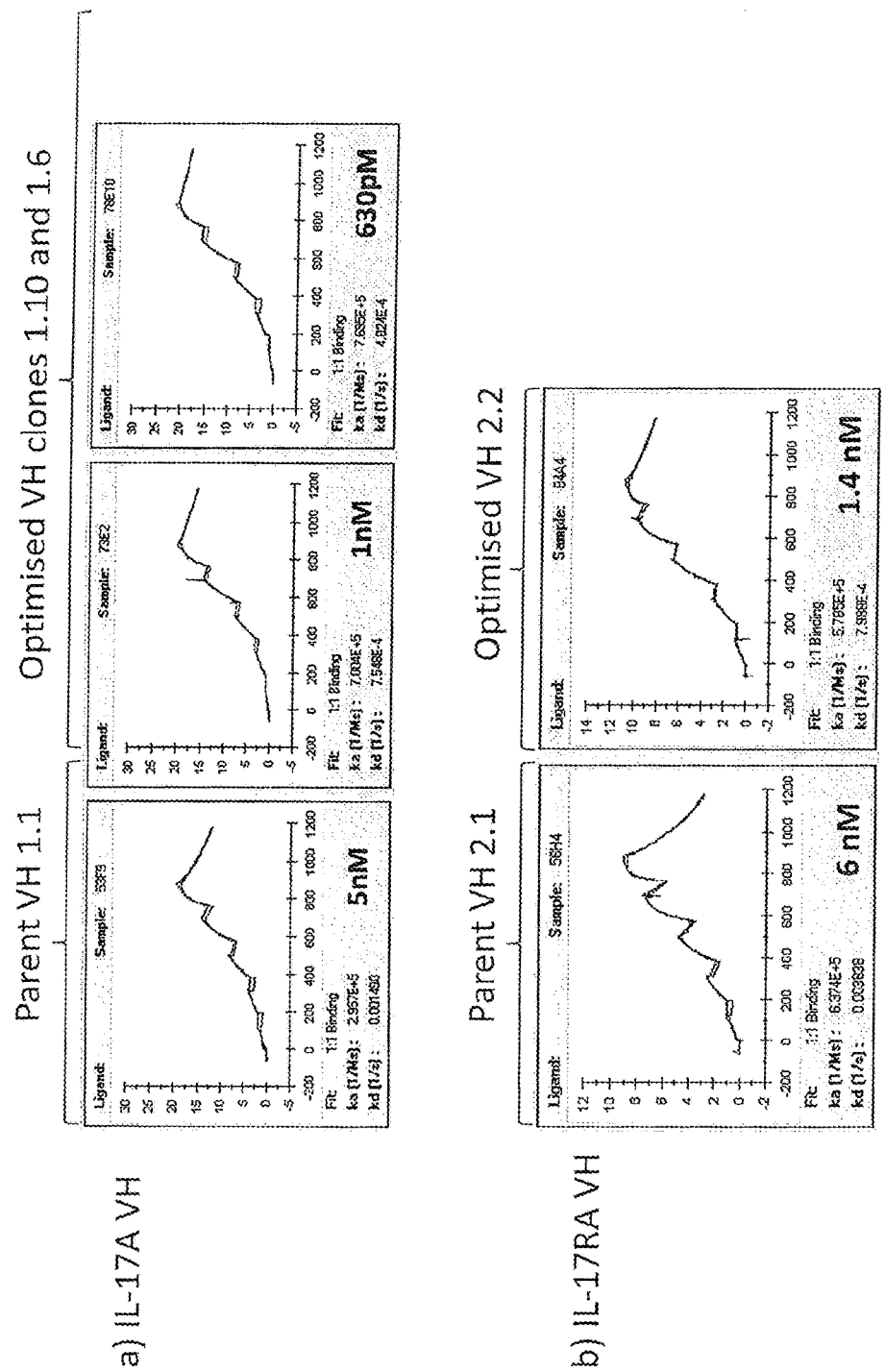
FIG. 6 shows BIAcore data showing the binding kinetics of optimized variants of the clone 1.1 and clone 2.1 $V_H$: (a) parent $V_H$ 1.1, optimized $V_H$ clones 1.10 and 1.6; (b) parent $V_H$ 2.1 and optimized $V_H$ 2.2.

Following BIAcore analysis, variants of clone 1.1 were isolated from the recombination libraries with up to 10-fold improved affinities for IL-17A (e.g., clones clone 1.10 and clone 1.6, FIG. 6 (a)). Similarly, for clone 2.1 a new variant was isolated (clone 2.2) that was improved in affinity for IL-17RA by 5-fold (FIG. 6 (b)).

Sequence Listing Information
$V_H$ Nucleic Acid Sequences 1.1
(SEQ ID NO: 9)
GAGGTGCAGCTGGTGGAGTCTGGGGGAGGCTTGGTCCAGCCTGGGGGGTC

CCTGAGACTCTCCTGTGCAGCCTCTGGATTCACCTTTAGTAGTTATTCGA

TGTACTGGGTCCGCCAGGCTCCAGGGAAGGGGCTGGAGTGGGTGGCCAAC

ATAAAGCAAGATGGAAGTGAGAAATACTATGTGGACTCTGTGAAGGGCCG

ATTCACCATCTCCAGAGACAACGCCAAGAACTCACTGTTTCTGCAAATGA

ATAGCCTGAGAGCCGAGGACACGGCTGTGTATTACTGTGCGAAAGGGGAA

ATACTACCCCTCCACTTTGACTACTGGGGCCAGGGAACCCTGGTCACTGT

CTCCTCA 1.6

(SEQ ID NO: 10)

GAGGTGCAGCTGGTGGAGTCTGGGGGAGGCTTGGTCCAGCCTGGGGGGTC

CCTGAGACTCTCCTGTGCAGCCTCTGGATTCACCTTTAGTAGTTATAGCA

TGTACTGGGTCCGCCAGGCTCCAGGGAAGGGCTGGAGTGGGTGGCCGAG

ATAAAGCAAGATGGAAGTGAGCAATACTATGTGGACTCTGTGAAGGGCCG

ATTCACCATCTCCAGAGACAACGCCAAGAACTCACTGTATCTGCAAATGA

ATAGCCTGAGAGCCGAGGACACGGCTGTGTATTACTGTGCGAAAGGGGAA

ATACTACCCCTCTACTTTGACTACTGGGGCCAGGGAACCCTGGTCACCGT

CTCCTCA 1.10

(SEQ ID NO: 11)

GAGGTGCAGCTGGTGGAGTCTGGGGGAGGCTTGGTCCAGCCTGGGGGGTC

CCTGAGACTCTCCTGTGCAGCCTCTGGATTCACCTTTAGTAGTTATCGCA

TGTACTGGGTCCGCCAGGCTCCAGGGAAGGGGCTGGAGTGGGTGGCCAGC

ATAGAACAAGATGGAAGTGAGGAATACTATGTGGACTCTGTGAAGGGCCG

ATTCACCATCTCCAGAGACAACGCCAAGAAGTCACTGTTTCTGCAAATGA

ATAGCCTGAGAGCCGAGGACACGGCTGTGTATTACTGTGCGAAAGGGGAA

ATACTACCCCTCTACTTTGACTACTGGGGCCAGGGAACCCTGGTCACTGT

CTCTTCA 2.1

(SEQ ID NO: 12)

CAGGTCCAGCTGGTGCAGTCTGGGGCTGAGGTGAAGAAGCCTGGGGCCTC

AGTGAAGGTCTCCTGCAAGGCTTCTGGATACCCCTTCACCAGTTATGATA

TCAATTGGGTGCGACAGGCCACAGGACAAAGCCTTGAGTGGATGGGATGG

ATGAACCCTAACAGTGGTGACACAGTCTATGCACAGAAATTCCAGGGCAG

AGTCACCATGACCAGGAATACCTCCATAAGCACAGCCTACATGGAGCTGA

GCAGCCTGAGATCTGAGGACACGGCCGTGTATTTTTGTGCGAGAGGCAGA

AGGGATGACTGGAAGAACAATTATTGGGGCCAGGGAACCCTGGTCACTGT

CTCCTCA 2.2

(SEQ ID NO: 13)

CAGGTCCAGCTGGTGCAGTCTGGGGCTGAGGTGAAGAAGCCTGGGGCCTC

AGTGAAGGTCTCCTGCAAGGCTTCTGGATACCCCTTCACCAGTTATGATA

TCAATTGGGTGCGACAGGCCACAGGACGAAGCCTTGAGTGGATGGGATGG

ATGAACCCTACCAATGGTAACACAGTCTATGCACAGAAATTCCAGGACAG

AGTCACCATGACCAGGAATACCTCCATAAGCACAGCCTACATGGAGCTGA

GCAGCCTGAGATCTGAGGACACGGCCGTGTATTTTTGTGCGAGAGGCAGA

AGGGATGACTGGAAGAACAATTATTGGGGCCAGGGAACCCTGGTCACTGT

CTCCTCA

TABLE 5

| $V_H$ amino acid sequences | | | | | | | |
|---|---|---|---|---|---|---|---|
| Clone | FR1 | CDR1 | FR2 | CDR2 | FR3 | CDR3 | FR4 |
| 1.1 | EVQLVESGGGLVQ PGGSLRLSCAASG FTFS (SEQ ID NO: 30) | SYSMY (SEQ ID NO: 31) | WVRQAPG KGLEWVA (SEQ ID NO: 32) | NIKQDGSEK YYVDSVKG (SEQ ID NO: 33) | RFTISRDNAKNSLFLQ MNSLRAEDTAVYYCA K (SEQ ID NO: 34) | GEILPLHF DY (SEQ ID NO: 35) | WGQGTL VTVSS (SEQ ID NO: 36) |
| 1.6 | EVQLVESGGGLVQ PGGSLRLSCAASG FTFS (SEQ ID NO: 37) | SYSMY (SEQ ID NO: 38) | WVRQAPG KGLEWVA SEQ ID NO: 39) | EIKQDGSEQ YYVDSVKG (SEQ ID NO: 40) | RFTISRDNAKNSLYL QMNSLRAEDTAVYY CAK (SEQ ID NO: 41) | GEILPLYF DY (SEQ ID NO: 42) | WGQGTL VTVSS (SEQ ID NO: 43) |
| 1.10 | EVQLVESGGGLVQ PGGSLRLSCAASG FTFS (SEQ ID NO: 44) | SYRMY (SEQ ID NO: 45) | WVRQAPG KGLEWVA (SEQ ID NO: 46) | SIEQDGSEEY YVDSVKG (SEQ ID NO: 47) | RFTISRDNAKKSLFLQ MNSLRAEDTAVYYCA K (SEQ ID NO: 48) | GEILPLYF DY (SEQ ID NO: 49) | WGQGTL VTVSS (SEQ ID NO: 50) |
| 2.1 | QVQLVQSGAEVKK PGASVKVSCKASG YPFT (SEQ ID NO: 51) | SYDIN (SEQ ID NO: 52) | WVRQATG QSLEWMG (SEQ ID NO: 53) | WMNPNSGD TVYAQKFQG (SEQ ID NO: 54) | RVTMTRNTSISTAYM ELSSLRSEDTAVYFC AR (SEQ ID NO: 55) | GRRDDW KNNY (SEQ ID NO: 56) | WGQGTL VTVSS (SEQ ID NO: 57) |
| 2.2 | QVQLVQSGAEVKK PGASVKVSCKASG YPFT (SEQ ID NO: 58) | SYDIN (SEQ ID NO: 59) | WVRQATG RSLEWMG (SEQ ID NO: 60) | WMNPTNGNT VYAQKFQD (SEQ ID NO: 61) | RVTMTRNTSISTAYM ELSSLRSEDTAVYFC AR (SEQ ID NO: 62) | GRRDDW KNNY (SEQ ID NO: 63) | WGQGTL VTVSS (SEQ ID NO: 64) |

The invention claimed is:

1. A method of designing an immunoglobulin library for optimisation of a biological property of a first lead immunoglobulin, the method comprising:
   a) identifying one or more related immunoglobulins of common lineage with and that bind the same target antigen as the first lead immunoglobulin, said one or more related immunoglobulins being related to the first lead immunoglobulin, each immunoglobulin having been raised against a target antigen by immunisation of a transgenic non-human mammal comprising human immunoglobulin genes with the target antigen and said one or more related immunoglobulins being derived from the same germline sequence by somatic hypermutation of a germline sequence in the transgenic non-human mammal;
   b) comparing amino acid sequences of the first lead immunoglobulin and the one or more related immunoglobulins;
   c) identifying, based on the sequence comparison, one or more sites at which there are variant amino acid residues between:
   (i) the first lead immunoglobulin and the one or more related immunoglobulins, and/or (ii) where the one or more related immunoglobulins is a plurality of immunoglobulins, between the plurality of immunoglobulins, wherein the one or more sites at which there are variant amino acid residues comprise somatic hypermutation hot spots targeted during the immune response that are potential sites for modification of the first lead immunoglobulin;

d) selecting one or more sites for modification to replace an amino acid of the first lead immunoglobulin with the corresponding variant amino acid of one or more of the related immunoglobulins, based on the sequence comparison; and e) generating nucleic acid molecules comprising immunoglobulin-encoding nucleotide sequences for the library based on the sequence of the first lead immunoglobulin, modified at one or more of the selected sites for modification.

2. The method of claim 1, wherein the one or more related immunoglobulins are of common lineage and bind the same target antigen as the first lead immunoglobulin, optionally with at least 70%, 80%, 85%, 90%, 95% homology in at least one CDR region to the lead immunoglobulin.

3. The method of claim 1, wherein the one or more related immunoglobulins have at least 70% homology in CDR3 to the lead immunoglobulin and/or wherein the one or more related immunoglobulins have at least 70% homology in CDR1 and/or CDR2 to the lead immunoglobulin and/or wherein the one or more related immunoglobulins have at least 70% homology in the framework regions to the lead immunoglobulin.

4. The method of claim 1 wherein step c) comprises identifying sites for modification within the CDRs of the immunoglobulin sequences, wherein a site within the CDRs is considered a site for modification if there is a variant amino acid residue present in at least one, two, three, four, or five of the related immunoglobulins.

5. The method of claim 1 wherein step c) further comprises identifying sites for modification outside the CDRs of the immunoglobulin sequences, wherein a site outside the CDRs is considered a site for modification if there is a variant amino acid residue present in at least 20% of the related immunoglobulins, optionally wherein a site outside the CDRs which would otherwise be identified as a site for modification is not identified as a site for modification if modifying the site would lead to the introduction of one or more of the following features into the modified immunoglobulin: (i) unpaired cysteines, (ii) oxidation sites (free methionines), (iii) glycosylation sites, (iv) deamidation sites, and (v) isomerisation sites.

6. The method of claim 1, further comprising step f) generating an immunoglobulin library comprising immunoglobulins having the sequences generated in step e), optionally further comprising step g) screening the immunoglobulin library to identify one or more immunoglobulins having desired biological properties.

7. The method of claim 1, comprising, prior to step a), the step α) of generating and sequencing a plurality of immunoglobulins, including a first lead immunoglobulin and one or more related immunoglobulins, optionally wherein the plurality of immunoglobulins is generated by immunizing a non-human mammal, optionally a mouse or rat, optionally a transgenic mouse or rat expressing human immunoglobulin genes, with a target antigen.

8. The method of claim 1, comprising, prior to step a), the step β) of identifying a first lead immunoglobulin.

9. The method of claim 1 wherein the immunoglobulins are antibodies, or antigen-binding fragments of an antibody, optionally wherein the immunoglobulins comprise or consist of heavy chain only antibodies or wherein the immunoglobulins comprise or consist of $V_H$ domains of antibodies.

10. A method of optimising a lead immunoglobulin, the method comprising:

A) performing the method of claim 1; and

B) selecting one or more optimised immunoglobulins from the library based on a desired property of the optimised immunoglobulin.

\* \* \* \* \*

SEQUENCE LISTING

<160> NUMBER OF SEQ ID NOS: 123

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
ggattgttat tactcgcggc ccag                                            24

<210> SEQ ID NO 2
<211> LENGTH: 28
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 11
<223> OTHER INFORMATION: /note="n = a, c, t or g"

<400> SEQUENCE: 2
ctggtgaagg ngtatccaga agccttgc                                        28

<210> SEQ ID NO 3
<211> LENGTH: 93
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 18
<223> OTHER INFORMATION: /note="n = a, c, t or g"
<220> FEATURE:
<221> NAME/KEY: misc_feature
<222> LOCATION: 28
<223> OTHER INFORMATION: /note="G or C"
<220> FEATURE:
<221> NAME/KEY: misc_feature
<222> LOCATION: 31
<223> OTHER INFORMATION: /note="A or T"
<220> FEATURE:
<221> NAME/KEY: misc_feature
<222> LOCATION: 64
<223> OTHER INFORMATION: /note="A or G"

<400> SEQUENCE: 3
gcaaggcttc tggatacncc ttcaccantt ntgatatcaa ttgggtgcga caggccacag     60
gacnaagcct tgagtggatg ggatggatga acc                                  93

<210> SEQ ID NO 4
<211> LENGTH: 70
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 20
<223> OTHER INFORMATION: /note="C or T"
<220> FEATURE:
<221> NAME/KEY: misc_feature
<222> LOCATION: 41
<223> OTHER INFORMATION: /note="A or C or T"
<220> FEATURE:
<221> NAME/KEY: misc_feature
<222> LOCATION: 44
<223> OTHER INFORMATION: /note="C or T"

```
<220> FEATURE:
<221> NAME/KEY: misc_feature
<222> LOCATION: 46
<223> OTHER INFORMATION: /note="C or G or T"
<220> FEATURE:
<221> NAME/KEY: misc_feature
<222> LOCATION: 47
<223> OTHER INFORMATION: /note="C or G or T"
<220> FEATURE:
<221> NAME/KEY: misc_feature
<222> LOCATION: 48
<223> OTHER INFORMATION: /note="C or T"

<400> SEQUENCE: 4
cctggtcatg gtgactctgn cctggaattt ctgtgcatag ncantnnnag ggttcatcca     60
tcccatccac                                                            70

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
ggcagagtca ccatgaccag gaa                                             23

<210> SEQ ID NO 6
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 12
<223> OTHER INFORMATION: /note="C or T"
<220> FEATURE:
<221> NAME/KEY: misc_feature
<222> LOCATION: 20
<223> OTHER INFORMATION: /note="A or C"

<400> SEQUENCE: 6
gttcttccag tnatcccttn tgcctctcgc ac                                   32

<210> SEQ ID NO 7
<211> LENGTH: 32
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 13
<223> OTHER INFORMATION: /note="G or T"
<220> FEATURE:
<221> NAME/KEY: misc_feature
<222> LOCATION: 21
<223> OTHER INFORMATION: /note="A or G"

<400> SEQUENCE: 7
gtgcgagagg canaagggat nactggaaga ac                                   32

<210> SEQ ID NO 8
<211> LENGTH: 20
<212> TYPE: DNA
<213> ORGANISM: Artificial Sequence
<220> FEATURE:
<223> OTHER INFORMATION: primer
```

```
<400> SEQUENCE: 8
ccgtggtgat ggtggtgatg                                                    20

<210> SEQ ID NO 9
<211> LENGTH: 357
<212> TYPE: DNA
<213> ORGANISM: Homo sapiens

<400> SEQUENCE: 9
gaggtgcagc tggtggagtc tgggggaggc ttggtccagc ctgggggtc cctgagactc         60 tcctgtgcag cctctggatt cacctttagt agttattcga tgtactgggt ccgccaggct       120
ccagggaagg ggctggagtg ggtggccaac ataaagcaag atggaagtga aaatactat        180 gtggactctg tgaagggccg attcaccatc tccagagaca acgccaagaa ctcactgttt       240
ctgcaaatga atagcctgag agccgaggac acggctgtgt attactgtgc gaaaggggaa       300
atactacccc tccactttga ctactggggc cagggaaccc tggtcactgt ctcctca         357

<210> SEQ ID NO 10
<211> LENGTH: 357
<212> TYPE: DNA
<213> ORGANISM: Homo sapiens

<400> SEQUENCE: 10
gaggtgcagc tggtggagtc tgggggaggc ttggtccagc ctgggggtc cctgagactc         60 tcctgtgcag cctctggatt cacctttagt agttatagca tgtactgggt ccgccaggct       120
ccagggaagg ggctggagtg ggtggccgag ataaagcaag atggaagtga gcaatactat       180
gtggactctg tgaagggccg attcaccatc tccagagaca acgccaagaa ctcactgtat       240
ctgcaaatga atagcctgag agccgaggac acggctgtgt attactgtgc gaaaggggaa       300
atactacccc tctactttga ctactggggc cagggaaccc tggtcaccgt ctcctca         357

<210> SEQ ID NO 11
<211> LENGTH: 357
<212> TYPE: DNA
<213> ORGANISM: Homo sapiens

<400> SEQUENCE: 11
gaggtgcagc tggtggagtc tgggggaggc ttggtccagc ctgggggtc cctgagactc         60 tcctgtgcag cctctggatt cacctttagt agttatcgca tgtactgggt ccgccaggct       120
ccagggaagg ggctggagtg ggtggccagc atagaacaag atggaagtga ggaatactat       180
gtggactctg tgaagggccg attcaccatc tccagagaca acgccaagaa gtcactgttt       240
ctgcaaatga atagcctgag agccgaggac acggctgtgt attactgtgc gaaaggggaa       300
atactacccc tctactttga ctactggggc cagggaaccc tggtcactgt ctcttca         357

<210> SEQ ID NO 12
<211> LENGTH: 357
<212> TYPE: DNA
<213> ORGANISM: Homo sapiens

<400> SEQUENCE: 12
caggtccagc tggtgcagtc tggggctgag gtgaagaagc ctggggcctc agtgaaggtc         60
tcctgcaagg cttctggata cccttcacc agttatgata tcaattgggt gcgacaggcc       120
acaggacaaa gccttgagtg gatgggatgg atgaaccta acagtggtga cacagtctat       180
gcacagaaat tccagggcag agtcaccatg accaggaata cctccataag cacagcctac       240
```

```
atggagctga gcagcctgag atctgaggac acggccgtgt attttgtgc gagaggcaga      300 agggatgact ggaagaacaa ttattggggc cagggaaccc tggtcactgt ctcctca       357
```

<210> SEQ ID NO 13
<211> LENGTH: 357
<212> TYPE: DNA
<213> ORGANISM: Homo sapiens

<400> SEQUENCE: 13

```
caggtccagc tggtgcagtc tggggctgag gtgaagaagc ctggggcctc agtgaaggtc      60
tcctgcaagg cttctggata ccccttcacc agttatgata tcaattgggt gcgacaggcc     120
acaggacgaa gccttgagtg gatgggatgg atgaaccta ccaatggtaa cacagtctat     180
gcacagaaat tccaggacag agtcaccatg accaggaata cctccataag cacagcctac     240
atggagctga gcagcctgag atctgaggac acggccgtgt attttgtgc gagaggcaga      300 agggatgact ggaagaacaa ttattggggc cagggaaccc tggtcactgt ctcctca       357
```

<210> SEQ ID NO 14
<211> LENGTH: 73
<212> TYPE: DNA
<213> ORGANISM: Artificial Sequence
<220> FEATURE:
<223> OTHER INFORMATION: primer

<400> SEQUENCE: 14

```
gccgctggat tgttattact cgcggcccag ccggccatgg cccaggtbca gctggtgcag      60
tctggggctg agg                                                        73
```

<210> SEQ ID NO 15
<211> LENGTH: 65
<212> TYPE: DNA
<213> ORGANISM: Artificial Sequence
<220> FEATURE:
<223> OTHER INFORMATION: primer

<400> SEQUENCE: 15

```
gccgctggat tgttattact cgcggcccag ccggccatgg cccagatcac cttgaaggag      60
tctgg                                                                 65
```

<210> SEQ ID NO 16
<211> LENGTH: 71
<212> TYPE: DNA
<213> ORGANISM: Artificial Sequence
<220> FEATURE:
<223> OTHER INFORMATION: primer

<400> SEQUENCE: 16

```
gccgctggat tgttattact cgcggcccag ccggccatgg ccsaggtgca gctggtggag      60
tctgggggag g                                                          71
```

<210> SEQ ID NO 17
<211> LENGTH: 65
<212> TYPE: DNA
<213> ORGANISM: Artificial Sequence
<220> FEATURE:
<223> OTHER INFORMATION: primer

<400> SEQUENCE: 17

```
gccgctggat tgttattact cgcggcccag ccggccatgg cccaggtgca gctgcaggag      60
``` tcggg                                                             65

<210> SEQ ID NO 18
<211> LENGTH: 65
<212> TYPE: DNA
<213> ORGANISM: Artificial Sequence
<220> FEATURE:
<223> OTHER INFORMATION: primer

<400> SEQUENCE: 18
gccgctggat tgttattact cgcggcccag ccggccatgg cccaggtaca gctgcagcag    60
tcagg                                                             65

<210> SEQ ID NO 19
<211> LENGTH: 54
<212> TYPE: DNA
<213> ORGANISM: Artificial Sequence
<220> FEATURE:
<223> OTHER INFORMATION: primer

<400> SEQUENCE: 19
ccgtggtgat ggtggtgatg gctaccgcca ccctcgagtg argagacrgt gacc          54

<210> SEQ ID NO 20
<211> LENGTH: 71
<212> TYPE: DNA
<213> ORGANISM: Artificial Sequence
<220> FEATURE:
<223> OTHER INFORMATION: primer

<400> SEQUENCE: 20
gccgctggat tgttattact cgcggcccag ccggccatgg ccsaggtgca gctggtggag    60
tctgggggag g                                                      71

<210> SEQ ID NO 21
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 18
<223> OTHER INFORMATION: /note="any base"
<220> FEATURE:
<221> NAME/KEY: misc_feature
<222> LOCATION: 19
<223> OTHER INFORMATION: /note="C or T"
<220> FEATURE:
<221> NAME/KEY: misc_feature
<222> LOCATION: 20
<223> OTHER INFORMATION: /note="C or G or T"

<400> SEQUENCE: 21
tggcggaccc agtacatnnn ataactacta aaggtg                            36

<210> SEQ ID NO 22
<211> LENGTH: 36
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 17
<223> OTHER INFORMATION: /note="A or C or G"
<220> FEATURE:
<221> NAME/KEY: misc_feature
<222> LOCATION: 18
<223> OTHER INFORMATION: /note="A or G"
<220> FEATURE:
<221> NAME/KEY: misc_feature
<222> LOCATION: 19
<223> OTHER INFORMATION: /note="any base"

<400> SEQUENCE: 22
cacctttagt agttatnnna tgtactgggt ccgcca         36

<210> SEQ ID NO 23
<211> LENGTH: 51
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 12
<223> OTHER INFORMATION: /note="C or G or T"
<220> FEATURE:
<221> NAME/KEY: misc_feature
<222> LOCATION: 28
<223> OTHER INFORMATION: /note="any base"
<220> FEATURE:
<221> NAME/KEY: misc_feature
<222> LOCATION: 30
<223> OTHER INFORMATION: /note="C or T"
<220> FEATURE:
<221> NAME/KEY: misc_feature
<222> LOCATION: 34
<223> OTHER INFORMATION: /note="G or C"
<220> FEATURE:
<221> NAME/KEY: misc_feature
<222> LOCATION: 35
<223> OTHER INFORMATION: /note="C or T"
<220> FEATURE:
<221> NAME/KEY: misc_feature
<222> LOCATION: 36
<223> OTHER INFORMATION: /note="C or T"

<400> SEQUENCE: 23
cacatagtat tnctcacttc catcttgntn tatnnnggcc acccactcca g         51

<210> SEQ ID NO 24
<211> LENGTH: 37
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 16
<223> OTHER INFORMATION: /note="A or C or G"

<400> SEQUENCE: 24
caagatggaa gtgagnaata ctatgtggac tctgtga         37

<210> SEQ ID NO 25
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 19
<223> OTHER INFORMATION: /note="A or T"
<220> FEATURE:
<221> NAME/KEY: misc_feature
<222> LOCATION: 27
<223> OTHER INFORMATION: /note="G or C"

<400> SEQUENCE: 25
aggctattca tttgcagana cagtganttc ttggcgttgt ctctg    45

<210> SEQ ID NO 26
<211> LENGTH: 45
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 19
<223> OTHER INFORMATION: /note="G or C"
<220> FEATURE:
<221> NAME/KEY: misc_feature
<222> LOCATION: 27
<223> OTHER INFORMATION: /note="A or T"

<400> SEQUENCE: 26
cagagacaac gccaagaant cactgtntct gcaaatgaat agcct    45

<210> SEQ ID NO 27
<211> LENGTH: 36
<212> TYPE: DNA
<213> ORGANISM: Artificial Sequence
<220> FEATURE:
<223> OTHER INFORMATION: primer

<400> SEQUENCE: 27
agtatttccc ctttcgcaca gtaatacaca gccgtg    36

<210> SEQ ID NO 28
<211> LENGTH: 67
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 44
<223> OTHER INFORMATION: /note="C or T"
<220> FEATURE:
<221> NAME/KEY: misc_feature
<222> LOCATION: 46
<223> OTHER INFORMATION: /note="G or C"
<220> FEATURE:
<221> NAME/KEY: misc_feature
<222> LOCATION: 53
<223> OTHER INFORMATION: /note="C or T"

<400> SEQUENCE: 28
cacggctgtg tattactgtg cgaaagggga aatactaccc ctcnantttg acnactgggg    60
ccaggga    67

<210> SEQ ID NO 29
<211> LENGTH: 54
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 42
<223> OTHER INFORMATION: /note="A or G"
<220> FEATURE:
<221> NAME/KEY: misc_feature
<222> LOCATION: 48
<223> OTHER INFORMATION: /note="A or G"

<400> SEQUENCE: 29

```
ccgtggtgat ggtggtgatg gctaccgcca ccctcgagtg angagacngt gacc         54
```

<210> SEQ ID NO 30
<211> LENGTH: 30
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 31
<211> LENGTH: 5
<212> TYPE: PRT
<213> ORGANISM: Homo sapiens

<400> SEQUENCE: 31

Ser Tyr Ser Met Tyr
1               5

<210> SEQ ID NO 32
<211> LENGTH: 14
<212> TYPE: PRT
<213> ORGANISM: Homo sapiens

<400> SEQUENCE: 32

Trp Val Arg Gln Ala Pro Gly Lys Gly Leu Glu Trp Val Ala
1               5                   10

<210> SEQ ID NO 33
<211> LENGTH: 17
<212> TYPE: PRT
<213> ORGANISM: Homo sapiens

<400> SEQUENCE: 33

Asn Ile Lys Gln Asp Gly Ser Glu Lys Tyr Tyr Val Asp Ser Val Lys
1               5                   10                  15

Gly

<210> SEQ ID NO 34
<211> LENGTH: 32
<212> TYPE: PRT
<213> ORGANISM: Homo sapiens

<400> SEQUENCE: 34

Arg Phe Thr Ile Ser Arg Asp Asn Ala Lys Asn Ser Leu Phe Leu Gln
1               5                   10                  15

Met Asn Ser Leu Arg Ala Glu Asp Thr Ala Val Tyr Tyr Cys Ala Lys
            20                  25                  30

<210> SEQ ID NO 35
<211> LENGTH: 10
<212> TYPE: PRT
<213> ORGANISM: Homo sapiens

<400> SEQUENCE: 35

Gly Glu Ile Leu Pro Leu His Phe Asp Tyr
1               5                   10

<210> SEQ ID NO 36

<211> LENGTH: 11
<212> TYPE: PRT
<213> ORGANISM: Homo sapiens

<400> SEQUENCE: 36

Trp Gly Gln Gly Thr Leu Val Thr Val Ser Ser
1               5                   10

<210> SEQ ID NO 37
<211> LENGTH: 30
<212> TYPE: PRT
<213> ORGANISM: Homo sapiens

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 38
<211> LENGTH: 5
<212> TYPE: PRT
<213> ORGANISM: Homo sapiens

<400> SEQUENCE: 38

Ser Tyr Ser Met Tyr
1               5

<210> SEQ ID NO 39
<211> LENGTH: 14
<212> TYPE: PRT
<213> ORGANISM: Homo sapiens

<400> SEQUENCE: 39

Trp Val Arg Gln Ala Pro Gly Lys Gly Leu Glu Trp Val Ala
1               5                   10

<210> SEQ ID NO 40
<211> LENGTH: 17
<212> TYPE: PRT
<213> ORGANISM: Homo sapiens

<400> SEQUENCE: 40

Glu Ile Lys Gln Asp Gly Ser Glu Gln Tyr Tyr Val Asp Ser Val Lys
1               5                   10                  15

Gly

<210> SEQ ID NO 41
<211> LENGTH: 32
<212> TYPE: PRT
<213> ORGANISM: Homo sapiens

<400> SEQUENCE: 41

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 42
<211> LENGTH: 10
<212> TYPE: PRT
<213> ORGANISM: Homo sapiens

<400> SEQUENCE: 42

Gly Glu Ile Leu Pro Leu Tyr Phe Asp Tyr
1               5                   10

<210> SEQ ID NO 43
<211> LENGTH: 11
<212> TYPE: PRT
<213> ORGANISM: Homo sapiens

<400> SEQUENCE: 43

Trp Gly Gln Gly Thr Leu Val Thr Val Ser Ser
1               5                   10

<210> SEQ ID NO 44
<211> LENGTH: 29
<212> TYPE: PRT
<213> ORGANISM: Homo sapiens

<400> SEQUENCE: 44

Val Gln Leu Val Glu Ser Gly Gly Leu Val Gln Pro Gly Gly Ser
1               5                   10                  15

Leu Arg Leu Ser Cys Ala Ala Ser Gly Phe Thr Phe Ser
            20                  25

<210> SEQ ID NO 45
<211> LENGTH: 5
<212> TYPE: PRT
<213> ORGANISM: Homo sapiens

<400> SEQUENCE: 45

Ser Tyr Arg Met Tyr
1               5

<210> SEQ ID NO 46
<211> LENGTH: 14
<212> TYPE: PRT
<213> ORGANISM: Homo sapiens

<400> SEQUENCE: 46

Trp Val Arg Gln Ala Pro Gly Lys Gly Leu Glu Trp Val Ala
1               5                   10

<210> SEQ ID NO 47
<211> LENGTH: 17
<212> TYPE: PRT
<213> ORGANISM: Homo sapiens

<400> SEQUENCE: 47

Ser Ile Glu Gln Asp Gly Ser Glu Tyr Tyr Val Asp Ser Val Lys
1               5                   10                  15

Gly

<210> SEQ ID NO 48
<211> LENGTH: 32
<212> TYPE: PRT
<213> ORGANISM: Homo sapiens

<400> SEQUENCE: 48

Arg Phe Thr Ile Ser Arg Asp Asn Ala Lys Lys Ser Leu Phe Leu Gln
1               5                   10                  15

Met Asn Ser Leu Arg Ala Glu Asp Thr Ala Val Tyr Tyr Cys Ala Lys
            20                  25                  30

```
<210> SEQ ID NO 49
<211> LENGTH: 10
<212> TYPE: PRT
<213> ORGANISM: Homo sapiens

<400> SEQUENCE: 49

Gly Glu Ile Leu Pro Leu Tyr Phe Asp Tyr
1               5                   10

<210> SEQ ID NO 50
<211> LENGTH: 11
<212> TYPE: PRT
<213> ORGANISM: Homo sapiens

<400> SEQUENCE: 50

Trp Gly Gln Gly Thr Leu Val Thr Val Ser Ser
1               5                   10

<210> SEQ ID NO 51
<211> LENGTH: 30
<212> TYPE: PRT
<213> ORGANISM: Homo sapiens

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr
            20                  25                  30

<210> SEQ ID NO 52
<211> LENGTH: 5
<212> TYPE: PRT
<213> ORGANISM: Homo sapiens

<400> SEQUENCE: 52

Ser Tyr Asp Ile Asn
1               5

<210> SEQ ID NO 53
<211> LENGTH: 14
<212> TYPE: PRT
<213> ORGANISM: Homo sapiens

<400> SEQUENCE: 53

Trp Val Arg Gln Ala Thr Gly Gln Ser Leu Glu Trp Met Gly
1               5                   10

<210> SEQ ID NO 54
<211> LENGTH: 17
<212> TYPE: PRT
<213> ORGANISM: Homo sapiens

<400> SEQUENCE: 54

Trp Met Asn Pro Asn Ser Gly Asp Thr Val Tyr Ala Gln Lys Phe Gln
1               5                   10                  15

Gly

<210> SEQ ID NO 55
<211> LENGTH: 32
<212> TYPE: PRT
<213> ORGANISM: Homo sapiens

<400> SEQUENCE: 55

Arg Val Thr Met Thr Arg Asn Thr Ser Ile Ser Thr Ala Tyr Met Glu
```

```
                1               5                  10                 15
Leu Ser Ser Leu Arg Ser Glu Asp Thr Ala Val Tyr Phe Cys Ala Arg
                20                 25                 30
```

<210> SEQ ID NO 56
<211> LENGTH: 10
<212> TYPE: PRT
<213> ORGANISM: Homo sapiens

<400> SEQUENCE: 56

```
Gly Arg Arg Asp Asp Trp Lys Asn Asn Tyr
1               5                   10
```

<210> SEQ ID NO 57
<211> LENGTH: 11
<212> TYPE: PRT
<213> ORGANISM: Homo sapiens

<400> SEQUENCE: 57

```
Trp Gly Gln Gly Thr Leu Val Thr Val Ser Ser
1               5                   10
```

<210> SEQ ID NO 58
<211> LENGTH: 30
<212> TYPE: PRT
<213> ORGANISM: Homo sapiens

<400> SEQUENCE: 58

```
Gln Val Gln Leu Val Gln Ser Gly Ala Glu Val Lys Lys Pro Gly Ala
1               5                   10                 15
Ser Val Lys Val Ser Cys Lys Ala Ser Gly Tyr Pro Phe Thr
                20                 25                 30
```

<210> SEQ ID NO 59
<211> LENGTH: 5
<212> TYPE: PRT
<213> ORGANISM: Homo sapiens

<400> SEQUENCE: 59

```
Ser Tyr Asp Ile Asn
1               5
```

<210> SEQ ID NO 60
<211> LENGTH: 14
<212> TYPE: PRT
<213> ORGANISM: Homo sapiens

<400> SEQUENCE: 60

```
Trp Val Arg Gln Ala Thr Gly Arg Ser Leu Glu Trp Met Gly
1               5                   10
```

<210> SEQ ID NO 61
<211> LENGTH: 17
<212> TYPE: PRT
<213> ORGANISM: Homo sapiens

<400> SEQUENCE: 61

```
Trp Met Asn Pro Thr Asn Gly Asn Thr Val Tyr Ala Gln Lys Phe Gln
1               5                   10                 15
Asp
```

<210> SEQ ID NO 62
<211> LENGTH: 32

<212> TYPE: PRT
<213> ORGANISM: Homo sapiens

<400> SEQUENCE: 62

```
Arg Val Thr Met Thr Arg Asn Thr Ser Ile Ser Thr Ala Tyr Met Glu
1               5                   10                  15
Leu Ser Ser Leu Arg Ser Glu Asp Thr Ala Val Tyr Phe Cys Ala Arg
            20                  25                  30
```

<210> SEQ ID NO 63
<211> LENGTH: 10
<212> TYPE: PRT
<213> ORGANISM: Homo sapiens

<400> SEQUENCE: 63

```
Gly Arg Arg Asp Asp Trp Lys Asn Asn Tyr
1               5                   10
```

<210> SEQ ID NO 64
<211> LENGTH: 11
<212> TYPE: PRT
<213> ORGANISM: Homo sapiens

<400> SEQUENCE: 64

```
Trp Gly Gln Gly Thr Leu Val Thr Val Ser Ser
1               5                   10
```

<210> SEQ ID NO 65
<211> LENGTH: 31
<212> TYPE: DNA
<213> ORGANISM: Artificial Sequence
<220> FEATURE:
<223> OTHER INFORMATION: primer

<400> SEQUENCE: 65
ctcgagggtg gcggtagcca tcaccaccat c                              31

<210> SEQ ID NO 66
<211> LENGTH: 29
<212> TYPE: DNA
<213> ORGANISM: Artificial Sequence
<220> FEATURE:
<223> OTHER INFORMATION: Primer

<400> SEQUENCE: 66
tccatggcca tcgccggctg ggccgcgag                                 29

<210> SEQ ID NO 67
<211> LENGTH: 119
<212> TYPE: PRT
<213> ORGANISM: Homo sapiens

<400> SEQUENCE: 67

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ser Met Tyr Trp Val Arg Gln Ala Pro Gly Lys Gly Leu Glu Trp Val
        35                  40                  45
Ala Asn Ile Lys Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Phe
65                  70                  75                  80
```

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 68
<211> LENGTH: 119
<212> TYPE: PRT
<213> ORGANISM: Homo sapiens

<400> SEQUENCE: 68

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Met Phe Ser Ser Tyr
            20                  25                  30

Gly Met Tyr Trp Val Arg Gln Ala Pro Gly Lys Gly Leu Glu Trp Val
        35                  40                  45

Ala Asn Ile Glu Gln Asp Gly Ser Glu Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 69
<211> LENGTH: 119
<212> TYPE: PRT
<213> ORGANISM: Homo sapiens

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Met Phe Ser Ser Tyr
            20                  25                  30

Gly Met Tyr Trp Val Arg Gln Ala Pro Gly Lys Gly Leu Glu Trp Val
        35                  40                  45

Ala Asn Ile Glu Gln Asp Gly Ser Glu Lys Tyr Tyr Val Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu His Phe Asp Tyr Trp Gly Gln Gly
            100                 105                 110

Thr Leu Val Thr Val Ser Ser
        115

<210> SEQ ID NO 70
<211> LENGTH: 119
<212> TYPE: PRT
<213> ORGANISM: Homo sapiens

<400> SEQUENCE: 70

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Phe Thr Phe Ser Ser Tyr
            20                  25                  30

Gly Met Tyr Trp Val Arg Gln Ala Pro Gly Lys Gly Leu Glu Trp Val
            35                  40                  45

Ala Asn Ile Lys Gln Asp Gly Ser Glu Gln Tyr Tyr Val Asp Ser Val
        50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu His Phe Asp Tyr Trp Gly Gln Gly
            100                 105                 110

Thr Leu Val Thr Val Ser Ser
            115

<210> SEQ ID NO 71
<211> LENGTH: 119
<212> TYPE: PRT
<213> ORGANISM: Homo sapiens

<400> SEQUENCE: 71

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Ser Met Tyr Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Lys Gly Glu Ile Leu Pro Leu His Phe Asp Tyr Trp Gly Gln Gly
            100                 105                 110

Thr Leu Val Thr Val Ser Ser
            115

<210> SEQ ID NO 72
<211> LENGTH: 118
<212> TYPE: PRT
<213> ORGANISM: Homo sapiens

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Arg Met Tyr Trp Val Arg Gln Ala Pro Gly Lys Gly Leu Glu Trp Val
            35                  40                  45

Ala Ser Ile Asn Gln Asp Gly Ser Glu Lys Tyr Tyr Val Asp Ser Val
        50                  55                  60

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Met Tyr Tyr Cys
                 85                  90                  95

Ala Lys Gly Glu Ile Leu Pro Leu His Phe Asp Tyr Arg Gly Gln Gly
            100                 105                 110

Thr Leu Val Thr Val Ser
            115

<210> SEQ ID NO 73
<211> LENGTH: 119
<212> TYPE: PRT
<213> ORGANISM: Homo sapiens

<400> SEQUENCE: 73

Gln Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Ser Tyr
            20                  25                  30

Glu Met Tyr Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Met Tyr Tyr Cys
                 85                  90                  95

Ala Lys Gly Glu Ile Leu Pro Leu His Phe Asp Tyr Arg Gly Gln Gly
            100                 105                 110

Thr Leu Val Thr Val Ser Ser
            115

<210> SEQ ID NO 74
<211> LENGTH: 119
<212> TYPE: PRT
<213> ORGANISM: Homo sapiens

<400> SEQUENCE: 74

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ser Met Ile Trp Val Arg Gln Ala Pro Gly Lys Gly Leu Glu Trp Val
         35                  40                  45

Ala Asp Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 75
<211> LENGTH: 119
```

<212> TYPE: PRT
<213> ORGANISM: Homo sapiens

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Ile Trp Val Arg Gln Ala Pro Gly Lys Gly Leu Glu Trp Val
        35                  40                  45

Ala Asp Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Tyr Phe Asp Tyr Trp Gly Gln Gly
            100                 105                 110

Thr Leu Val Thr Val Ser Ser
            115

<210> SEQ ID NO 76
<211> LENGTH: 119
<212> TYPE: PRT
<213> ORGANISM: Homo sapiens

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Leu Leu Tyr
65                  70                  75                  80

Leu Gln Met Asn Ser Leu Arg Val Glu Asp Thr Ala Val Tyr Tyr Cys
                85                  90                  95

Ala Lys Gly Glu Ile Leu Pro Leu Tyr Phe Asp Tyr Arg Gly Gln Gly
            100                 105                 110

Thr Leu Val Thr Val Ser Ser
            115

<210> SEQ ID NO 77
<211> LENGTH: 119
<212> TYPE: PRT
<213> ORGANISM: Homo sapiens

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val

```
                    50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Tyr Phe Asp His Trp Gly Gln Gly
            100                 105                 110

Thr Leu Val Thr Val Ser Ser
            115

<210> SEQ ID NO 78
<211> LENGTH: 119
<212> TYPE: PRT
<213> ORGANISM: Homo sapiens

<400> SEQUENCE: 78

Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Thr Phe Ser Asn Tyr
                20                  25                  30

Ser Met Tyr Trp Val Arg Gln Ala Pro Gly Lys Gly Leu Glu Trp Val
             35                  40                  45

Ala Asn Ile Lys Gln Asp Gly Ser Glu Glu Tyr Tyr Val Asp Ser Val
 50                  55                  60

Lys Gly Arg Phe Thr Ile Ser Arg Asp Asn Ala Arg Asn Ser Leu Tyr
 65                  70                  75                  80

Leu Gln Met Ile Ser Leu Arg Ala Glu Asp Thr Ala Val Tyr Tyr Cys
                 85                  90                  95

Ala Lys Gly Glu Ile Leu Pro Leu Tyr Phe Asp His Trp Gly Gln Gly
            100                 105                 110

Thr Leu Val Thr Val Ser Ser
            115

<210> SEQ ID NO 79
<211> LENGTH: 119
<212> TYPE: PRT
<213> ORGANISM: Homo sapiens

<400> SEQUENCE: 79

Glu Val Gln Leu Val Glu Ser Gly Gly Gly Leu Val Gln Pro Gly Gly
 1               5                  10                  15

Ser Leu Arg Leu Ser Cys Thr Ala Ser Gly Phe Thr Phe Ser Asn Tyr
                20                  25                  30

Ser Met Tyr Trp Val Arg Gln Ala Pro Gly Lys Gly Leu Glu Trp Val
             35                  40                  45

Ala Asn Ile Lys Gln Asp Gly Ser Glu Glu Tyr Tyr Val Asp Ser Val
 50                  55                  60

Lys Gly Arg Phe Thr Ile Ser Arg Asp Asn Ala Arg Asn Ser Leu Tyr
 65                  70                  75                  80

Leu Gln Met Ile Ser Leu Arg Ala Glu Asp Thr Ala Val Tyr Tyr Cys
                 85                  90                  95

Ala Lys Gly Glu Ile Leu Pro Leu Tyr Phe Asp His Trp Gly Gln Gly
            100                 105                 110

Thr Leu Val Thr Val Ser Ser
            115
```

<210> SEQ ID NO 80
<211> LENGTH: 119
<212> TYPE: PRT
<213> ORGANISM: Homo sapiens

<400> SEQUENCE: 80

Gln Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Asn Tyr
            20                  25                  30

Ser Met Tyr Trp Val Arg Gln Ala Pro Gly Lys Gly Leu Glu Trp Val
        35                  40                  45

Ala Asn Ile Lys Gln Asp Gly Ser Glu Glu Tyr Tyr Val Asp Ser Val
    50                  55                  60

Lys Gly Arg Phe Thr Ile Ser Arg Asp Asn Ala Arg Asn Ser Leu Tyr
65                  70                  75                  80

Leu Gln Met Ile Ser Leu Arg Ala Glu Asp Thr Ala Val Tyr Tyr Cys
                85                  90                  95

Ala Lys Gly Glu Ile Leu Pro Leu Tyr Phe Asp His Trp Gly Gln Gly
            100                 105                 110

Thr Leu Val Thr Val Ser Ser
        115

<210> SEQ ID NO 81
<211> LENGTH: 119
<212> TYPE: PRT
<213> ORGANISM: Homo sapiens

<400> SEQUENCE: 81

Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115

<210> SEQ ID NO 82
<211> LENGTH: 119
<212> TYPE: PRT
<213> ORGANISM: Homo sapiens

<400> SEQUENCE: 82

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Gln Phe Asp Tyr Trp Gly Gln Gly
            100                 105                 110

Thr Leu Val Thr Val Ser Ser
            115

<210> SEQ ID NO 83
<211> LENGTH: 119
<212> TYPE: PRT
<213> ORGANISM: Homo sapiens

<400> SEQUENCE: 83

Glu Val Gln Leu Val Glu Ser Gly Gly Gly Leu Val Gln Arg Gly Gly
 1               5                  10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro Leu Gln Phe Asp Tyr Trp Gly Gln Gly
            100                 105                 110

Thr Leu Val Thr Val Ser Ser
            115

<210> SEQ ID NO 84
<211> LENGTH: 119
<212> TYPE: PRT
<213> ORGANISM: Homo sapiens

<400> SEQUENCE: 84

Gln Val Gln Leu Val Glu Ser Gly Gly Gly Met Val Gln Pro Gly Gly
 1               5                  10                  15

Ser Leu Arg Leu Ser Cys Ala Val Ser Gly Phe Thr Phe Ser Ser Tyr
            20                  25                  30

Arg Met Tyr Trp Val Arg Gln Ala Pro Gly Lys Gly Leu Glu Trp Val
        35                  40                  45

Ala Ser Ile Asn Gln Asp Gly Ser Glu Lys Tyr Tyr Val Asp Ser Val
            50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Met Tyr Tyr Cys
                 85                  90                  95

Ala Lys Gly Glu Ile Leu Pro Leu His Phe Asp Tyr Arg Gly Gln Gly
            100                 105                 110

Thr Leu Val Thr Val Ser Ser
            115

-continued

<210> SEQ ID NO 85
<211> LENGTH: 119
<212> TYPE: PRT
<213> ORGANISM: Homo sapiens

<400> SEQUENCE: 85

```
Gln Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Asn Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115
```

<210> SEQ ID NO 86
<211> LENGTH: 119
<212> TYPE: PRT
<213> ORGANISM: Homo sapiens

<400> SEQUENCE: 86

```
Glu Val Gln Leu Val Glu Ser Gly Gly Gly Leu Val Gln Arg Gly Gly
1               5                   10                  15

Ser Leu Arg Leu Ser Cys Ala Ala Ser Gly Phe Thr Phe Ser Ser Tyr
            20                  25                  30

Trp Met Tyr Trp Val Arg Gln Ala Pro Gly Lys Gly Leu Glu Trp Val
        35                  40                  45

Ala Lys Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Lys Gly Glu Ile Leu Pro Leu Gln Phe Asp Tyr Trp Gly Gln Gly
            100                 105                 110

Thr Leu Val Thr Val Ser Ser
        115
```

<210> SEQ ID NO 87
<211> LENGTH: 119
<212> TYPE: PRT
<213> ORGANISM: Homo sapiens

<400> SEQUENCE: 87

```
Gln Val Gln Leu Gln Glu Ser Gly Gly Asp Trp Val Gln Pro Gly Gly
1               5                   10                  15

Ser Leu Arg Leu Ser Cys Gly Ala Ser Gly Phe Thr Phe Ser Ser Tyr
            20                  25                  30
```

Trp Met Tyr Trp Val Arg Gln Ala Pro Gly Lys Gly Leu Glu Trp Val
            35                  40                  45

Ala Lys Ile Lys Gln Asp Gly Thr Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Gly Glu Ile Leu Pro His Tyr Phe Asp Tyr Trp Gly Gln Gly
            100                 105                 110

Thr Leu Val Thr Val Ser Ser
        115

<210> SEQ ID NO 88
<211> LENGTH: 119
<212> TYPE: PRT
<213> ORGANISM: Homo sapiens

<400> SEQUENCE: 88

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Pro Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Asn Ser Gly Asp Thr Val Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 89
<211> LENGTH: 119
<212> TYPE: PRT
<213> ORGANISM: Homo sapiens

<400> SEQUENCE: 89

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Pro Phe Thr Ser Tyr
            20                  25                  30

Asp Ile Asn Trp Val Arg Gln Ala Ala Gly Gln Ser Leu Glu Trp Met
        35                  40                  45

Gly Trp Met Asn Pro Asn Ser Gly Asn Thr Val Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Gly Arg Arg Asp Asp Trp Lys Asn Asn Tyr Trp Gly Gln Gly
            100                 105                 110

```
Thr Leu Val Thr Val Ser Ser
        115

<210> SEQ ID NO 90
<211> LENGTH: 119
<212> TYPE: PRT
<213> ORGANISM: Homo sapiens

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Thr Tyr
            20                  25                  30

Asp Ile Asn Trp Val Arg Gln Ala Thr Gly Gln Ser Leu Glu Trp Met
        35                  40                  45

Gly Trp Met Asn Pro Asn Ser Gly Asp Thr Val Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 91
<211> LENGTH: 119
<212> TYPE: PRT
<213> ORGANISM: Homo sapiens

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Asn Asn Gly Asn Thr Val Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 92
<211> LENGTH: 119
<212> TYPE: PRT
<213> ORGANISM: Homo sapiens

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
            20                  25                  30
Asp Ile Asn Trp Val Arg Gln Ala Thr Gly Gln Ser Leu Glu Trp Met
            35                  40                  45

Gly Trp Met Asn Pro Asn Ser Gly Asp Thr Val Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
                100                 105                 110

Thr Leu Val Thr Val Ser Ser
            115

<210> SEQ ID NO 93
<211> LENGTH: 119
<212> TYPE: PRT
<213> ORGANISM: Homo sapiens

<400> SEQUENCE: 93

Gln Val Gln Leu Val Gln Ser Gly Ala Glu Val Lys Arg Pro Gly Ala
 1               5                  10                  15

Ser Val Lys Val Ser Cys Lys Ala Ser Gly Tyr Pro Phe Thr Ser Tyr
            20                  25                  30

Asp Ile Asn Trp Val Arg Gln Ala Thr Gly Gln Ser Leu Glu Trp Met
            35                  40                  45

Gly Trp Met Asn Pro Asn Ser Gly Asn Thr Val Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
                100                 105                 110

Thr Leu Val Thr Val Ser Ser
            115

<210> SEQ ID NO 94
<211> LENGTH: 119
<212> TYPE: PRT
<213> ORGANISM: Homo sapiens

<400> SEQUENCE: 94

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
            35                  40                  45

Gly Trp Met Asn Pro Lys Ser Gly Asp Thr Val Tyr Ala Gln Lys Phe
     50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Phe Cys
                85                  90                  95

Ala Arg Gly Ile Arg Asp Asp Trp Lys Asn Asn Tyr Trp Gly Gln Gly
```

-continued

```
                  100                 105                 110

Thr Leu Val Thr Val Ser Ser
        115

<210> SEQ ID NO 95
<211> LENGTH: 119
<212> TYPE: PRT
<213> ORGANISM: Homo sapiens

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Ser Thr Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Tyr Thr Val Tyr Ala Gln Lys Phe
    50                  55                  60

Gln Gly Arg Val Ala Met Thr Arg Asn Thr Ser Leu Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Gly Ile Arg Asp Asp Trp Lys Asn Asn Tyr Trp Gly Gln Gly
            100                 105                 110

Thr Leu Val Thr Val Ser Ser
        115

<210> SEQ ID NO 96
<211> LENGTH: 119
<212> TYPE: PRT
<213> ORGANISM: Homo sapiens

<400> SEQUENCE: 96

Gln Val Gln Leu Val Gln Ser Gly Ala Glu Val Lys Lys Pro Gly Ala
1               5                   10                  15

Ser Val Arg Val Ser Cys Lys Ala Ser Gly Tyr Thr Phe Thr Ser Tyr
            20                  25                  30

Asp Ile Asn Trp Val Arg Gln Ala Thr Gly Arg Ser Leu Glu Trp Met
        35                  40                  45

Gly Trp Met Asn Pro Asp Ser Gly Tyr Thr Val Tyr Ala Gln Lys Phe
    50                  55                  60

Gln Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 97
<211> LENGTH: 119
<212> TYPE: PRT
<213> ORGANISM: Homo sapiens

<400> SEQUENCE: 97

Gln Val Gln Leu Val Gln Ser Gly Ala Glu Val Lys Lys Pro Gly Ala
1               5                   10                  15
```

-continued

Ser Val Ile Val Ser Cys Lys Ala Ser Gly Tyr Thr Phe Thr Ser Tyr
            20                  25                  30

Asp Ile Asn Trp Val Arg Gln Ala Thr Gly Arg Ser Leu Glu Trp Met
        35                  40                  45

Gly Trp Met Asn Pro Asn Ser Gly Asp Thr Val Tyr Ala Gln Lys Phe
50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 98
<211> LENGTH: 119
<212> TYPE: PRT
<213> ORGANISM: Homo sapiens

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Asp Ile Asn Trp Val Arg Gln Ala Thr Gly Arg Ser Leu Glu Trp Met
        35                  40                  45

Gly Trp Met Asn Pro Asn Ser Gly Asp Thr Val Tyr Ala Gln Lys Phe
50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 99
<211> LENGTH: 119
<212> TYPE: PRT
<213> ORGANISM: Homo sapiens

<400> SEQUENCE: 99

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Glu Ser Gly Tyr Thr Val Tyr Ala Gln Lys Phe
50                  55                  60

Gln Gly Arg Val Ala Met Thr Arg Asn Thr Ser Leu Thr Thr Ala Tyr
65                  70                  75                  80

Met Glu Leu Ser Asn Leu Arg Ser Glu Asp Thr Ala Val Tyr Tyr Cys
                85                  90                  95

```
Ala Arg Gly Ile Arg Asp Asp Trp Lys Asn Asn Tyr Trp Gly Gln Gly
            100                 105                 110

Thr Leu Val Thr Val Ser Ser
        115

<210> SEQ ID NO 100
<211> LENGTH: 119
<212> TYPE: PRT
<213> ORGANISM: Homo sapiens

<400> SEQUENCE: 100

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Asn Ser Gly Tyr Thr Val Tyr Ala Gln Lys Phe
    50                  55                  60

Gln Asp Arg Val Thr Met Thr Arg Asn Ile Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 101
<211> LENGTH: 119
<212> TYPE: PRT
<213> ORGANISM: Homo sapiens

<400> SEQUENCE: 101

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Asn Asn Gly Asn Thr Val Tyr Ala Gln Gln Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 102
<211> LENGTH: 119
<212> TYPE: PRT
<213> ORGANISM: Homo sapiens

<400> SEQUENCE: 102
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Asp Ile Asn Trp Val Arg Gln Ala Thr Gly Gln Ser Leu Glu Trp Met
        35                  40                  45

Gly Trp Met Asn Pro Asn Ser Gly Asp Thr Val Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Thr Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 103
<211> LENGTH: 119
<212> TYPE: PRT
<213> ORGANISM: Homo sapiens

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Asp Ile Asn Trp Val Arg Gln Ala Thr Gly Gln Ser Leu Glu Trp Met
        35                  40                  45

Gly Trp Met Asn Pro Asn Ser Gly Asn Thr Val Tyr Ala Gln Lys Phe
    50                  55                  60

Gln Asp Arg Val Thr Met Thr Arg Asn Thr Ser Ile Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Gly Ile Arg Asp Asp Trp Lys Asn Asn Tyr Trp Gly Gln Gly
            100                 105                 110

Thr Leu Val Thr Val Ser Ser
        115

<210> SEQ ID NO 104
<211> LENGTH: 119
<212> TYPE: PRT
<213> ORGANISM: Homo sapiens

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Asp Thr Val Tyr Ala Gln Lys Phe
    50                  55                  60

Gln Gly Arg Val Ala Met Thr Arg Asn Thr Ser Ile Ser Thr Ala Tyr
65                  70                  75                  80

```
Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 105
<211> LENGTH: 119
<212> TYPE: PRT
<213> ORGANISM: Homo sapiens

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Asp Thr Val Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Thr Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 106
<211> LENGTH: 119
<212> TYPE: PRT
<213> ORGANISM: Homo sapiens

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Asp Thr Val Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Gly Ile Arg Asp Asp Trp Lys Asn Asn Tyr Trp Gly Gln Gly
            100                 105                 110

Thr Leu Val Thr Val Ser Ser
        115

<210> SEQ ID NO 107
<211> LENGTH: 119
<212> TYPE: PRT
<213> ORGANISM: Homo sapiens
```

-continued

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Asn Thr Val Tyr Ala Gln Lys Phe
    50                  55                  60

Gln Gly Arg Val Thr Met Thr Arg Asn Thr Ser Leu Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ile Arg Asp Asn Trp Lys Asn Asn Tyr Trp Gly Gln Gly
            100                 105                 110

Thr Leu Val Thr Val Ser Ser
        115

<210> SEQ ID NO 108
<211> LENGTH: 119
<212> TYPE: PRT
<213> ORGANISM: Homo sapiens

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Asn Thr Val Tyr Ala Gln Lys Phe
    50                  55                  60

Gln Gly Arg Val Thr Met Thr Arg Asn Thr Ser Leu Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ile Arg Asp Asn Trp Lys Asn Asn Tyr Trp Gly Gln Gly
            100                 105                 110

Thr Thr Val Thr Val Ser Ser
        115

<210> SEQ ID NO 109
<211> LENGTH: 119
<212> TYPE: PRT
<213> ORGANISM: Homo sapiens

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Asn Thr Val Tyr Ala Gln Lys Phe
    50                  55                  60

Gln Gly Arg Val Thr Met Thr Arg Asn Thr Ser Ile Ser Thr Ala Tyr 65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 110
<211> LENGTH: 119
<212> TYPE: PRT
<213> ORGANISM: Homo sapiens

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Lys Ser Gly Tyr Thr Val Tyr Ala Gln Lys Phe
    50                  55                  60

Gln Asp Arg Val Thr Met Thr Arg Asn Ile Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 111
<211> LENGTH: 119
<212> TYPE: PRT
<213> ORGANISM: Homo sapiens

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Asn Gly Asn Thr Val Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ile Ser Leu Thr Ser Glu Asp Thr Ala Val Tyr Tyr Cys
                85                  90                  95

Ala Arg Gly Arg Arg Asp Asn Trp Lys Asn Asn Tyr Trp Gly Gln Gly
            100                 105                 110

Thr Leu Val Thr Val Ser Ser
        115

<210> SEQ ID NO 112
<211> LENGTH: 119
<212> TYPE: PRT

<213> ORGANISM: Homo sapiens

<400> SEQUENCE: 112

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Asn Asn Gly Asn Ala Val Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 113
<211> LENGTH: 119
<212> TYPE: PRT
<213> ORGANISM: Homo sapiens

<400> SEQUENCE: 113

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Ser Ser Gly Tyr Thr Val Tyr Ala Gln Lys Phe
    50                  55                  60

Gln Asp Arg Val Thr Met Thr Arg Asn Ile Ser Ile Ser Thr Ala Tyr
65                  70                  75                  80

Met Glu Leu Ser Ser Leu Arg Ser Glu Asp Thr Ala Ile Tyr Phe Cys
                85                  90                  95

Ala Arg Gly Arg Arg Gly Asp Trp Lys Asn Asn Tyr Trp Gly Gln Gly
            100                 105                 110

Thr Leu Val Thr Val Ser Ser
        115

<210> SEQ ID NO 114
<211> LENGTH: 119
<212> TYPE: PRT
<213> ORGANISM: Homo sapiens

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Ser Ser Gly Tyr Thr Val Tyr Ala Gln Lys Phe
    50                  55                  60

Gln Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
            100                 105                 110

Thr Leu Val Thr Val Ser Ser
        115

<210> SEQ ID NO 115
<211> LENGTH: 119
<212> TYPE: PRT
<213> ORGANISM: Homo sapiens

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Ser Ser Gly Tyr Thr Val Tyr Ala Gln Lys Phe
    50                  55                  60

Gln Gly Arg Val Thr Met Thr Arg Asn Thr Ser Leu Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ile Arg Asp Asp Trp Lys Asn Asn Tyr Trp Gly Gln Gly
            100                 105                 110

Thr Leu Val Thr Val Ser Ser
        115

<210> SEQ ID NO 116
<211> LENGTH: 119
<212> TYPE: PRT
<213> ORGANISM: Homo sapiens

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Ser Leu Glu Trp Met
        35                  40                  45

Gly Trp Met Asn Pro Asp Ser Gly Tyr Thr Val Tyr Ala Gln Lys Phe
    50                  55                  60

Gln Asp Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Ile Arg Asp Asp Trp Lys Asn Asn Tyr Trp Gly Gln Gly
            100                 105                 110

Thr Leu Val Thr Val Ser Ser
        115

<210> SEQ ID NO 117

```
<211> LENGTH: 119
<212> TYPE: PRT
<213> ORGANISM: Homo sapiens

<400> SEQUENCE: 117

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Asp Ile Asn Trp Val Arg Gln Ala Thr Gly Gln Ser Leu Glu Trp Met
            35                  40                  45
Gly Trp Met Asn Pro Asp Ser Gly Tyr Thr Val Tyr Ala Gln Lys Phe
    50                  55                  60
Gln Asp Arg Val Thr Met Thr Arg Asn Thr Ser Ile Ser Thr Ala Tyr
65                  70                  75                  80
Met Glu Leu Ser Ser Leu Arg Ser Glu Asp Thr Ala Val Tyr Phe Cys
                85                  90                  95
Ala Arg Gly Arg Arg Asp Asp Trp Lys Asn Asn Tyr Trp Gly Gln Gly
            100                 105                 110
Thr Leu Val Thr Val Ser Ser
        115

<210> SEQ ID NO 118
<211> LENGTH: 119
<212> TYPE: PRT
<213> ORGANISM: Homo sapiens

<400> SEQUENCE: 118

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Asp Ile Asn Trp Val Arg Gln Ala Thr Gly Gln Ser Leu Glu Trp Met
            35                  40                  45
Gly Trp Met Asn Pro Thr Ser Gly Asn Thr Val Tyr Ala Gln Lys Phe
    50                  55                  60
Gln Asp Arg Val Thr Met Thr Arg Asn Thr Ser Ile Ser Thr Ala Tyr
65                  70                  75                  80
Met Glu Leu Ser Asn Leu Arg Ser Glu Asp Thr Ala Val Tyr Tyr Cys
                85                  90                  95
Ala Arg Gly Ile Arg Asp Asp Trp Lys Asn Asn Tyr Trp Gly Gln Gly
            100                 105                 110
Thr Leu Val Thr Val Ser Ser
        115

<210> SEQ ID NO 119
<211> LENGTH: 119
<212> TYPE: PRT
<213> ORGANISM: Homo sapiens

<400> SEQUENCE: 119

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
                20                  25                  30
Asp Ile Asn Trp Val Arg Gln Ala Thr Gly Gln Ser Leu Glu Trp Met
            35                  40                  45
```

```
Gly Trp Met Asn Pro Asn Ser Gly Asp Thr Val Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Thr Ser Glu Asp Thr Ala Val Tyr Tyr Cys
                85                  90                  95

Ala Arg Gly Arg Arg Asp Asp Trp Lys Asn Asn Tyr Trp Gly Gln Gly
                100                 105                 110

Thr Leu Val Thr Val Ser Ser
            115
```

<210> SEQ ID NO 120
<211> LENGTH: 119
<212> TYPE: PRT
<213> ORGANISM: Homo sapiens

<400> SEQUENCE: 120

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Ser Leu Glu Trp Met
            35                  40                  45

Gly Trp Met Asn Pro Asn Ser Gly Tyr Thr Val Tyr Ala Gln Lys Phe
        50                  55                  60

Gln Asp Arg Val Thr Met Thr Arg Asn Ile Ser Ile Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Arg Arg Asp Asp Trp Lys Asn Asn Tyr Trp Gly Gln Gly
                100                 105                 110

Thr Leu Val Thr Val Ser Ser
            115
```

<210> SEQ ID NO 121
<211> LENGTH: 119
<212> TYPE: PRT
<213> ORGANISM: Homo sapiens

<400> SEQUENCE: 121

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Ser Leu Glu Trp Met
            35                  40                  45

Gly Trp Met Asn Pro Asn Ser Gly Tyr Thr Val Tyr Ala Gln Lys Phe
        50                  55                  60

Gln Asp Arg Val Thr Met Thr Arg Asn Thr Ser Ile Ser Thr Ala Tyr
65                  70                  75                  80

Met Glu Leu Arg Asn Leu Arg Ser Glu Asp Thr Ala Val Tyr Phe Cys
                85                  90                  95

Ala Arg Gly Ile Arg Asp Asp Trp Lys Asn Asn Tyr Trp Gly Gln Gly
                100                 105                 110

Thr Leu Val Thr Val Ser Ser
            115
```

<210> SEQ ID NO 122
<211> LENGTH: 119
<212> TYPE: PRT
<213> ORGANISM: Homo sapiens

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Ser Leu Glu Trp Met
            35                  40                  45

Gly Trp Met Asn Pro Asn Ser Gly Asn Thr Val Tyr Ala Gln Lys Phe
    50                  55                  60

Gln Asp Arg Val Thr Met Thr Arg Asn Ile Ser Ile Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Gly Ile Arg Asp Asp Trp Lys Asn Asn Tyr Trp Gly Gln Gly
            100                 105                 110

Thr Leu Val Thr Val Ser Ser
        115

<210> SEQ ID NO 123
<211> LENGTH: 119
<212> TYPE: PRT
<213> ORGANISM: Homo sapiens

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Ser Leu Glu Trp Met
            35                  40                  45

Gly Trp Met Asn Pro Asn Ser Gly Asn Thr Val Tyr Ala Gln Lys Phe
    50                  55                  60

Gln Asp Arg Val Thr Met Thr Arg Asn Thr Ser Ile Ser Thr Ala Tyr
65                  70                  75                  80

Met Glu Leu Ser Asn Leu Arg Ser Glu Asp Thr Ala Val Tyr Tyr Cys
                85                  90                  95

Ala Arg Gly Ile Arg Asp Asp Trp Lys Asn Asn Tyr Trp Gly Gln Gly
            100                 105                 110

Thr Leu Val Thr Val Ser Ser
        115